(12) United States Patent
Chen et al.

(10) Patent No.: US 11,149,042 B2
(45) Date of Patent: Oct. 19, 2021

(54) PERFLUOROPOLYETHER GROUP-CONTAINING SILANE COMPOUND, PREPARATION METHOD THEREOF, SURFACE TREATMENT AGENT AND ARTICLE

(71) Applicant: GUANGZHOU UR MATERIALS TECHNOLOGY CO., LTD., Guangdong (CN)

(72) Inventors: Yijing Chen, Taiwan (CN); Qiguan Wang, Taiwan (CN)

(73) Assignee: GUANGZHOU UR MATERIALS TECHNOLOGY CO., LTD., Guangdong (CN)

( * ) Notice: Subject to any disclaimer, the term of this patent is extended or adjusted under 35 U.S.C. 154(b) by 0 days.

(21) Appl. No.: 17/019,167

(22) Filed: Sep. 11, 2020

(65) Prior Publication Data

US 2020/0407378 A1 Dec. 31, 2020

Related U.S. Application Data

(63) Continuation of application No. PCT/CN2018/087473, filed on May 18, 2018.

(30) Foreign Application Priority Data

May 16, 2018 (CN) .......................... 201810468845.1

(51) Int. Cl.
*C03C 17/30* (2006.01)
*C07F 7/18* (2006.01)
*C07F 7/08* (2006.01)

(52) U.S. Cl.
CPC ............ *C07F 7/1804* (2013.01); *C03C 17/30* (2013.01); *C07F 7/081* (2013.01); *C07F 7/1876* (2013.01); *C03C 2217/76* (2013.01); *C03C 2217/78* (2013.01); *C03C 2218/151* (2013.01)

(58) Field of Classification Search
CPC .... C03C 17/30; C09D 171/00; C08G 65/226; C08L 71/00
See application file for complete search history.

(56) References Cited

U.S. PATENT DOCUMENTS

| 6,200,684 | B1 * | 3/2001 | Yamaguchi | ............ C08G 65/00 428/447 |
| 7,196,212 | B2 | 3/2007 | Yamaguchi et al. | |
| 2015/0191629 | A1 | 7/2015 | Matsuda et al. | |

FOREIGN PATENT DOCUMENTS

| CN | 1703441 A | 11/2005 |
| CN | 101456947 A | 6/2009 |
| CN | 1902249 B | 6/2010 |
| CN | 101189278 B | 3/2012 |
| CN | 103201349 A | 7/2013 |
| CN | 106661436 A | 5/2017 |
| CN | 104769009 B | 8/2017 |
| CN | 107709506 A | 2/2018 |
| EP | 1 059 320 B1 | 7/2003 |
| JP | 11-29585 A | 2/1999 |
| JP | 2000-327772 A | 11/2000 |
| JP | 2014-5353 A | 1/2014 |

* cited by examiner

*Primary Examiner* — Kuo Liang Peng
(74) *Attorney, Agent, or Firm* — Seed IP Law Group LLP

(57) ABSTRACT

The present invention relates to a perfluoropolyether group-containing silane compound represented by formula (1): Rf—X$^1$—X$^2$—NQ$_k$T$_{2-k}$, (1), and a method for preparing the same. The present invention also relates to a perfluoropolyether group-containing silane compound represented by formula (2),

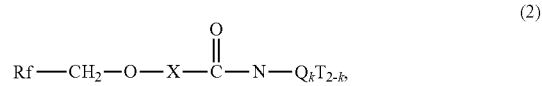

and a method for preparing the same. The present invention also relates to a perfluoropolyether group-containing silane compound represented by formula (3),

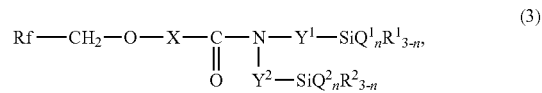

and a method for preparing the same. The perfluoropolyether group-containing silane compound of the present invention can be used for a surface treatment agent so that the substrates such as glass etc processed by the surface treatment agent are excellent in anti-fouling, anti-fingerprint, scrape resistant and abrasion resistant performances. Moreover, the preparation method of each of the compounds of the present invention is simple in process, easy to operate and implement.

27 Claims, 9 Drawing Sheets

PERFLUOROPOLYETHER GROUP-CONTAINING SILANE COMPOUND, PREPARATION METHOD THEREOF, SURFACE TREATMENT AGENT AND ARTICLE

CROSS-REFERENCE TO RELATED APPLICATIONS

This application is a bypass continuation application of International Application No. PCT/CN2018/087473, filed May 18, 2018, which claims priority to Chinese Application No. 201810468845.1, filed May 16, 2018, which applications are incorporated herein by reference in their entirety.

FIELD OF INVENTION

The present invention relates to a surface treatment agent, particularly to a perfluoropolyether group-containing silane compound and preparation method thereof, a surface treatment agent comprising the perfluoropolyether group-containing silane compound as well as an article treated using the surface treatment agent.

BACKGROUND OF THE INVENTION

It is known in the prior art that when a substrate is treated by a perfluoropolyether group-containing silane compound, a membrane layer, which has the properties of hydrophobicity, oleophobicity, anti-fouling, low coefficient of friction and durability, can be formed on the surface thereof. This is because that (1) perfluoropolyether in a molecule has the property of low surface energy, and (2) the siloxane group in a molecule can be bonded by dehydration condensation reaction to form a chemical bond on the surface of a substrate. A surface treatment agent containing the composition can be uniformly dispersed onto a substrate in the manner of spraying or vapor deposition, which forms a membrane layer having protection function via thermal curing. Since the membrane layer is only several nanometers thick and transparent, it will not influence the appearance and transparency of a substrate.

The membrane layer prepared with the existing perfluoropolyether group-containing silane compound has higher abrasion resistance, which can withstand reciprocating wear by steel wool over 5000 times, even up to ten thousands of times. The surface dynamic friction coefficient of the membrane layer can be reduced to 0.05 or so. However, there are many problems for the existing perfluoropolyether group-containing silane compound, such as big difficulty in synthesis process, many preparation steps, long preparation process, and raw materials with particular structure not easy to be obtained, thereby resulting in high price and high production cost.

SUMMARY

For the technical problem in the prior art, the present invention provides a new perfluoropolyether group-containing silane compound and a method for preparing the same.

In one aspect, the present invention provides a perfluoropolyether group-containing silane compound represented by formula (1):

In the formula, Rf is F—(CF$_2$)$_m$—(OC$_4$F$_8$)$_p$—(OC$_3$F$_6$)$_q$—(OC$_2$F$_4$)$_r$—(OCF$_2$)$_s$—OC(Z)F—(CF$_2$)$_t$—, here, p, q, r and s are separately independent and are integers of 0 or more and 200 or less, the sum of p, q, r and s is at least 1, the existing sequence and number of each repeating unit with p, q, r and s and bracketed with a brackets are arbitrary in the formula; m and t are separately integers of 0 or more and 30 or less, Z is F or CF$_3$;

wherein, said separately independent refers to that said letters present at each time in the chemical formula can be the same or different numerical values in the range thereof. For example, "p, q, r and s are separately independent and are integers of 0 or more and 20 or less" refers to that p, q, r and s present at each time in the chemical formula can represent as any same or different integers of 0 or more and 200 or less. It can be understood that the definition of separately independent hereinafter is the same as this.

X$^1$ is a bivalent organic group;

X$^2$ is carbonyl, sulfuryl or anhydride;

T, when present at each time, is separately independent and is hydroxyl, a hydrolysable group or hydrocarbon group;

Q, when present at each time, is separately independent and is —Y—SiR$^1$$_j$R$^2$$_{3-j}$; Y, when present at each time, is separately independent and is a bivalent organic group;

R$^1$, when present at each time, is separately independent and is alkoxy, hydroxyl or a group that can be hydrolyzed to hydroxyl group, wherein, preferably, R$^1$ is —OR$^3$, in the formula, R$^3$ is substituted or unsubstituted C$_{1-3}$alkyl, preferably, R$^3$ is methyl, ethyl, propyl, isopropyl;

R$^2$, when present at each time, is separately independent and is C$_{1-22}$ alkyl, or Q', Q' and Q has the same meaning, that is, Q', when present at each time, is also separately independently —Y—SiR$^1$$_j$R$^2$$_{3-j}$; it can be understood that Q' hereinafter has the same meaning as that of Q, and both are similar.

j is separately independent in each of Q and Q', that is, j in Q' and j in Q may be the same or different number value, being an integer selected from 0~3, the sum of j is 1 or more;

k is separately independently 1 or 2, preferably, k is 2.

In the above formula (1), Rf may also be the following formula (a) or (b):

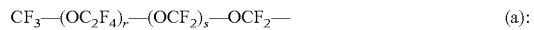

In the formula, the sum of r and s is an integer of 10 or more and 200 or less;

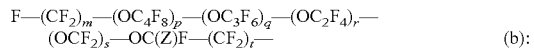

In the formula, m and t are separately independent, m is an integer of 1-16, t is an integer of 0-2, r and s are separately independent and are integers of 1 or more and 200 or less, the sum of p, q, r and s is 10 or more and 200 or less, the existing sequence and number of each repeating unit with p, q, r and s and bracketed with brackets are arbitrary in the formula.

In the above formula (1), X$^1$ may be a group as shown below:

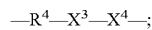

wherein, R$^4$ is C$_{1-6}$ alkyl or substituted C$_{1-6}$ alkyl; X$^3$ is a group selected from —O—, —S—, ortho, meta- or para-phenylene, ortho-, meta- or para-benzylidene, —C(O)O—, —CONR$^5$—, —O—CONR$^5$—, —Si(R$^6$)$_2$—, —(Si(R$^6$)$_2$O)$_f$—Si(R$^6$)$_2$— and —(CH$_2$)$_g$—; R$^5$, when present at each time, is separately independent and is a hydrogen atom, phenyl or C$_{1-6}$ alkyl; R$^6$ is C$_{1-6}$ alkyl or substituted C$_{1-6}$ alkyl; X$^4$ is a bivalent group; f, when present at each time, is separately independent and is an integer of 1~100, g, when present at each time, is separately independent and is an integer of 1~20;

Preferably, $X^4$ is a group represented by $-(R^7)_a-(X^5)_b-R^8-$, wherein:

$R^7$ is $-(CH_2)_c-$, ortho-, meta-, or para-phenylene, or ortho-, meta-, or para-benzylidene; c is an integer of 1~20; a is 0 or 1; b is 0 or 1;

$R^8$ is $-(CH_2)_d-$, ortho-, meta- or para-phenylene, or ortho-, meta-, or para-benzylidene; d is an integer of 1~20;

$X^5$ is $-(X^6)_e-$, $X^6$, when present at each time, is separately independent, and is a group selected from $-O-$, $-S-$, ortho-, meta- or para-phenylene, ortho-, meta- or para-benzylidene, $-C(O)O-$, $-CONR^5-$, $-O-CONR^5-$, $-Si(R^6)_2-$, $-(Si(R^6)_2O)_f-Si(R^6)_2-$ and $-(CH_2)_g-$; $R^5$, when present at each time, is separately independent, and is a hydrogen atom, phenyl or $C_{1-6}$ alkyl; $R^6$, when present at each time, is separately independent, and is phenyl or $C_{1-6}$ alkyl; f, when present at each time, is separately independent, and is an integer of 1~100; g, when present at each time, is separately independent, and is an integer of 1~20; e is an integer of 1~10.

In the above formula (1), T, when present at each time, is separately independent, and is selected from hydroxyl, $-O(R^7)$, $C_{1-12}$ alkyl, $C_{2-12}$ alkenyl, $C_{2-12}$ alkynyl and phenyl, $R^7$ is $C_{1-12}$ alkyl, preferably, T, when present at each time, is separately independent, and is hydroxyl, or $-O(R^7)$, $R^7$ is $C_{1-12}$ alkyl.

In another aspect, the present invention provides a perfluoropolyether group-containing silane compound having the following chemical general formula (2),

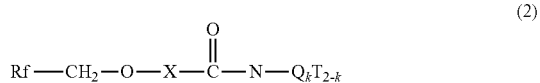

(2)

Wherein, Rf is

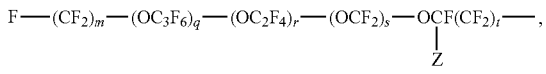

q, r and s are separately independent and are integers of 0 or more and 200 or less, the sum of q, r and s is at least 1, the existing sequence of each repeating unit noted with q, r or s and bracketed with brackets is arbitrary in the formula; in is an integer of 1-16, t is 0 or 1, Z is a fluoride atom or trifluoromethyl;

X is a bivalent organic group;

T, when present at each time, is separately independent and is hydroxyl, a hydrolysable group or hydrocarbon group;

Q, when present at each time, is separately independent and is $-Y-SiR^1_jR^2_{3-j}$;

Y, when present at each time, is separately independent and is a bivalent organic group;

$R^1$, when present at each time, is separately independent and is alkoxy, hydroxyl or a group that can be hydrolyzed to a hydroxyl group, wherein, preferably, it is alkoxy, and more preferably, $C_{1-3}$ alkoxy;

$R^2$, when present at each time, is separately independent and is $C_{1-22}$ alkyl or Q', Q' and Q have the same meaning;

j is separately independent in each of Q and Q', and is an integer selected from 0 to 3, the sum of j is at least 1;

k is separately independent, and is 1 or 2, preferably k is 2.

In the above formula (2), preferably, X is a group represented by $-(R^3)_a-(X^1)_b-R^4-$, wherein:

$R^3$ is $-(CH_2)_c-$, ortho-, meta- or para-phenylene, or ortho-, meta- or para-benzylidene; c is an integer of 1~20; a is 0 or 1;

$R^4$ is $-(CH_2)_d-$, ortho-, meta- or para-phenylene, or ortho-, meta- or para-benzylidene; d is an integer of 1~20;

$X^1$ is $-(X^2)_e-$;

b is 0 or 1;

$X^2$, when present at each time, is separately independent, and is a group selected from $-O-$, $-S-$, ortho-, meta- or para-phenylene, ortho-, meta- or para-benzylidene, $-C(O)O-$, $-CONR^5-$, $-O-CONR^5-$, $-Si(R^6)_2-$, $-(Si(R^6)_2O)_f-Si(R^6)_2-$ and $-(CH_2)_g-$; $R^5$, when present at each time, is separately independent, and is a hydrogen atom, phenyl or $C_{1-6}$ alkyl; $R^6$, when present at each time, is separately independent, and is phenyl or $C_{1-6}$ alkyl; f, when present at each time, is separately independent, and is an integer of 1~100; g, when present at each time, is separately independent, and is an integer of 1~20; e is an integer of 1~10.

In the above formula (2), preferably X is $C_{1-20}$ alkylidene, $-R^3-X^3-R^4-$ or $-X^4-R^4-$, wherein, $X^3$ is $-O-$, $-S-$, $-C(O)O-$, $-CONR^5-$, $-O-CONR^5-$, $-Si(R^6)_2-$, $-(Si(R^6)_2O)_f-Si(R^6)_2-$, $-O-(CH_2)_h-(Si(R^6)_2O)_f-Si(R^6)_2-$, $-CONR^5-(CH_2)_h-(Si(R^6)_2O)_f-Si(R^6)_2-$, $-CONR^5-(CH_2)_h-N(R^5)-$ or $-CONR^5$-(ortho-, meta- or para-phenylene)-$Si(R^6)_2-$; $X^4$ is $-S-$, $-C(O)O-$, $-CONR^5-$, $-O-CONR^5-(CH_2)_h-(Si(R^6)_2O)_f-Si(R^6)_2-$, $-CONR^5-(CH_2)_h-N(R^5)-$ or $-CONR^5$-(ortho-, meta- or para-phenylene)-$Si(R^6)_2-$; $R^3$ is $-(CH_2)_c-$, ortho-, meta- or para-phenylene, or ortho-, meta- or para-benzylidene; $R^4$ is $-(CH_2)_d-$, ortho-, meta- or para-phenylene, or ortho-, meta- or para-benzylidene; $R^5$, when present at each time, is separately independent, and is a hydrogen atom, phenyl or $C_{1-6}$ alkyl, $R^6$, when present at each time, is separately independent, and is phenyl or $C_{1-6}$ alkyl; h is an integer of 1~20; f, when present at each time, is separately independent, and is an integer of 1~100.

More preferably, $R^3$ is $-(CH_2)_c-$, $R^4$ is $-(CH_2)_d-$, wherein, c is an integer of 1~20; d is an integer of 1~20.

Further preferably, X is $C_{1-20}$ alkylidene, $-(CH_2)_c-O-(CH_2)_d-$, $-(CH_2)_c-(Si(R^6)_2O)_f-Si(R^6)_2-(CH_2)_d-$, $-(CH_2)_c-O-(CH_2)_h-(Si(R^6)_2O)_f-Si(R^6)_2-(CH_2)_d-$, c is an integer of 1~20; d is an integer of 1~20; $R^6$, when present at each time, is separately independent, and is phenyl or $C_{1-6}$ alkyl; h is an integer of 1~20; f, when present at each time, is separately independent, and is an integer of 1~100.

Further preferably, X is selected from the following groups: $-CH_2-$, $-(CH_2)_2-$, $-(CH_2)_3-$, $-(CH_2)_4-$, $-(CH_2)_6-$, $-CH_2C_6H_4-$, $-CH_2OCH_2-$, $-CH_2O(CH_2)_2-$, $-CH_2O(CH_2)_3-$, $-CH_2O(CH_2)_6-$, $-CH_2C_6H_4-OCH_2-$, $-CONH-(CH_2)_3-$, $-CON(CH_3)-(CH_2)_3-$, $-CON(Ph)-(CH_2)_3-$, Ph is phenyl, $-CON(CH_3)-(CH_2)_6-$, $-CON(Ph)-(CH_2)_6-$, Ph is phenyl, $-CONH-(CH_2)_2NH(CH_2)_3-$, $-CONH-(CH_2)_6NH(CH_2)_3-$, $-CH_2O-CONH-(CH_2)_3-$, $-CH_2O-CONH-(CH_2)_6-$, $-C(O)O-(CH_2)_3-$, $-C(O)O-(CH_2)_6-$, $-S-(CH_2)_3-$, $-(CH_2)_2S(CH_2)_3-$, $-CH_2O-(CH_2)_3Si(CH_3)_2OSi(CH_3)_2$ $-(CH_2)_2-$, $-CH_2O-(CH_2)_3Si(CH_3)_2OSi(CH_3)_2OSi(CH_3)_2(CH_2)_2-$, $-CH_2O-(CH_2)_3Si(CH_3)_2O(Si(CH_3)_2O)_2Si(CH_3)_2(CH_2)_2-$.

Preferably, T, when present at each time, is separately independent, and is selected from hydroxyl, $-O(R^7)$, $C_{1-12}$ alkyl, $C_{2-12}$ alkenyl, $C_{2-12}$ alkynyl and phenyl, $R^7$ is $C_{1-12}$ alkyl.

Further preferably, T, when present at each time, is separately independent, and is hydroxyl, or $-O(R^7)$, $R^7$ is $C_{1-12}$ alkyl.

Preferably, in Q of formula (2), j is 3.

Preferably, the perfluoropolyether group-containing silane compound as represented by the formula (2) has the number average molecule weight of 500-10,000, preferably 1000-8000, more preferably 3000-6000.

Still in another aspect, the present invention provides a perfluoropolyether group-containing silane compound having the following chemical general formula (3),

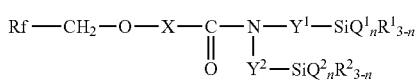   (3)

Wherein, Rf is $F-(CF_2)_m-(OC_3F_6)_q-(OC_2F_4)_r-(OCF_2)_s-OC(Z)F-(CF_2)_t-$, q, r, and s are separately independent and are integers of 0 or more and 200 or less, the sum of q, r and s is at least 1, the existing sequence of each repeating unit noted with q, r or s and bracketed with brackets is arbitrary in the formula; in is an integer of 1-16, t is 0 or 1, Z is a fluoride atom or trifluoromethyl;

X is a bivalent organic group, preferably X is $C_{1-6}$ alkylidene, $-CH_2C_6H_4-$ or $-CH_2C_6H_4-$ which has a substitutent on phenyl ring;

$Y^1$, $Y^2$ are separately independently $C_{1-6}$ alkylidene;

$Q^1$, $Q^2$ are separately independently alkoxy, hydroxyl or a group that can be hydrolyzed to hydroxyl group;

$R^1$, $R^2$ are separately independently $C_{1-6}$ alkyl or phenyl;

n is an integer of 1-3, preferably, n is 3.

Preferably, in the formula (3), Rf is $CF_3(OC_2F_4)_r(OCF_2)_sOCF_2$, wherein, r, s are separately independent and are integers of 0 or more and 200 or less, the sum of r, s is at least 1, the existing sequence of each repeating unit noted with r, s and bracketed with brackets is arbitrary in the formula;

X is $C_{1-6}$ alkylidene, $-CH_2C_6H_4-$ or $-CH_2C_6H_4-$ which has a substitutent on phenyl ring;

$Y^1$, $Y^2$ are separately independently $C_{1-6}$ alkylidene;

$Q^1$, $Q^2$ are separately independently alkoxy, hydroxyl or a group that can be hydrolyzed to hydroxyl group;

$R^1$, $R^2$ are separately independently $C_{1-6}$alkyl or phenyl.

Preferably, in the formula (3), X is $-CH_2-$, $-CH(CH_3)-$, $-C_2H_4-$, $-C_3H_6-$.

Preferably, in the formula (3), $Y^1$ and $Y^2$ are separately $-(CH_2)_3-$.

Preferably, in the formula (3), $Q^1$, $Q^2$ are separately independently $C_{1-6}$ alkoxy, more preferably, $Q^1$, $Q^2$ are separately independently $-OCH_3$, $-OCH(CH_3)_2$, $-OC_2H_5$ or $-OC_3H_7$.

Preferably, the perfluoropolyether group-containing silane compound as represented by the formula (3) has the number average molecule weight of 500-10,000, preferably 1000-8000, more preferably 3000-6000.

In one aspect, the present invention also provides a method for preparing a perfluoropolyether group-containing silane compound represented by the formula (1),

   (1);

which comprises:

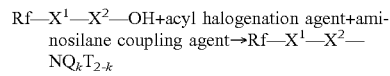

In the formula, Rf is $F-(CF_2)_m-(OC_4F_8)_p-(OC_3F_6)_q-(OC_2F_4)_r-(OCF_2)_s-OC(Z)F-(CF_2)_t-$, here, p, q, r and s are separately independent and are integers of 0 or more and 200 or less, the sum of p, q, r and s is at least 1, the existing sequence and number of each repeating unit with p, q, r and s and bracketed with brackets are arbitrary in the formula; in and t are separately integers of 0 or more and 30 or less, Z is F or $CF_3$;

$X^1$ is a bivalent organic group;

$X^2$ is carbonyl, sulfuryl or anhydride;

T, when present at each time, is separately independent and is hydroxyl, hydrolysable group or hydrocarbon group;

Q, when present at each time, is separately independent and is $-Y-SiR^1_jR^2_{3-j}$;

Y, when present at each time, is separately independent and is a bivalent organic group;

$R^1$, when present at each time, is separately independent and is alkoxy, hydroxyl or a group that can be hydrolyzed to hydroxyl group;

$R^2$, when present at each time, is separately independent and is $C_{1-22}$ alkyl or Q', wherein Q' and Q has the same meaning;

j is separately independent in each of Q and Q', being an integer selected from 0 to 3, the sum of j is 1 or more;

k is separately independent and is 1 or 2.

Preferably, acyl halogenation agent is $(COCl)_2$, $SOCl_2$, $POCl_3$, $PCl_5$ or $SOBr_2$.

Preferably, aminosilane coupling agent is $HNQ_kT_{2-k}$, the meaning of Q, T, k is the same as that defined in the above formula (1).

In another aspect, the present invention also provides a method for preparing a perfluoropolyether group-containing silane compound represented by the formula (2),

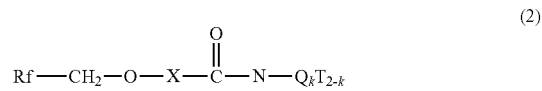   (2)

said method comprises:

reacting and converting a compound of formula $Rf-CH_2-O-X-COOH$ with acyl halogenation agent and aminosilane coupling agent to obtain a perfluoropolyether group-containing silane compound of formula (2),

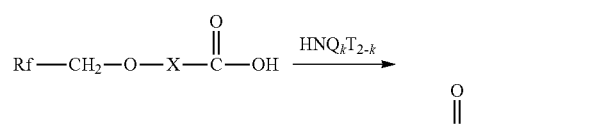

wherein, Rf is:

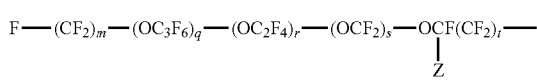

q, r and s are separately independent and are integers of 0 or more and 200 or less, the sum of p, q, r and s is at least 1, the existing sequence of each repeating unit noted with q, r or s and bracketed with brackets is arbitrary in the formula; in is an integer of 1-16, t is 0 or 1, Z is a fluoride atom or trifluoromethyl;

X is a bivalent organic group;

T, when present at each time, is separately independent and is hydroxyl, hydrolysable group or hydrocarbon group;

Q, when present at each time, is separately independent and is $—Y—SiR^1_jR^2_{3-k}$; Y, when present at each time, is separately independent and is a bivalent organic group; $R^1$, when present at each time, is separately independent and is alkoxy, hydroxyl or a group that can be hydrolyzed to hydroxyl group; $R^2$, when present at each time, is separately independent and is $C_{1-22}$ alkyl or Q', wherein Q' and Q have the same meaning; j is separately independent in each of Q and Q', and is an integer selected from 0~3, the sum of j is 1 or more;

k is separately independent, and is 1 or 2.

Preferably, the acyl halogenation agent is acyl halide, preferably acyl chloride, and more preferably oxalyl chloride.

Preferably, the aminosilane coupling agent is $HNQ_kT_{2-k}$, wherein Q is $—Y—SiR^1_jR^2_{3-j}$; Y is a bivalent organic group; R' is alkoxy, hydroxyl or a group that can be hydrolyzed to hydroxyl group; $R^2$ is $C_{1-22}$ alkyl or Q', wherein Q' and Q have the same meaning; j is separately independent in each of Q and Q', and is an integer selected from 0~3, the sum of j is a 1 or more; k is separately independent, and is 1 or 2.

Preferably, preparation of the starting raw material Rf—CH$_2$—O—X—COOH used in the forementioned reaction comprises:

Step 1: first reacting the compound of formula Rf—CH$_2$OH with a base in the presence of a solvent, and then making a nucleophilic substitution reaction with a compound of formula L-X-G, obtaining a compound of formula Rf—CH$_2$—O—X-G, wherein in the formula L-X-G, L is a leaving group or atom where a nucleophilic substitution reaction can occur, X is a bivalent organic group, G is a group that can be hydrolyzed to carboxylic acid,

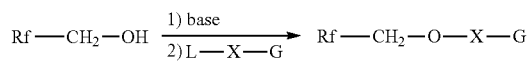

Step 2: chemically converting the compound of formula Rf—CH$_2$—O—X-G to obtain a compound of formula Rf—CH$_2$—O—X—COOH,

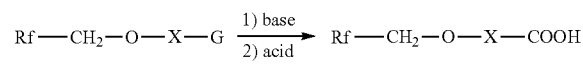

Preferably, the base in step 1 is selected from inorganic base or organic base; inorganic base is preferably selected from at least one of LiOH, NaOH, KOH, K$_2$CO$_3$, Na$_2$CO$_3$, Cs$_2$CO$_3$, NaH, t-BuOK; organic base is preferably selected from at least one of DIPEA (N,N-diisopropylethylamine), DBU (1,8-diazabicycloundec-7-ene), 1,1,3,3-tetramethylguanidine.

Preferably, in the compound of formula L-X-G of step 1, L is selected from: chlorine atom, bromine atom, iodine atom, or other leaving group(s) that can undergo nucleophilic substitution reaction; G is selected from: at least one group of ester group, nitrile group, amide group, or substituted amide group.

Preferably, the base in step 2 is selected from at least one of sodium hydroxide, potassium hydroxide, lithium hydroxide and cesium hydroxide.

Preferably, the acid in step 2 is selected from: hydrochloric acid, sulfuric acid, phosphoric acid or nitric acid.

Still in another aspect, the present invention also provides a method for preparing a perfluoropolyether group-containing silane compound represented by the formula (3),

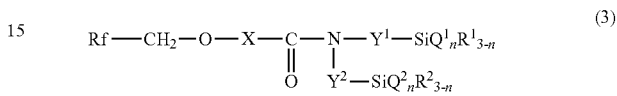

The method comprises: reacting Rf—CH$_2$—O—X—COOH with acyl halogenation agent and aminosilane coupling agent

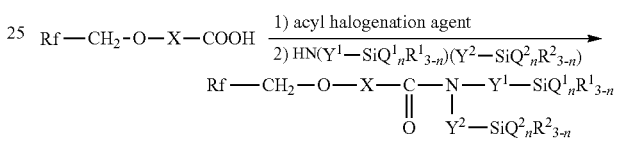

wherein, Rf is F—(CF$_2$)$_m$—(OC$_3$F$_6$)$_q$—(OC$_2$F$_4$)$_r$—(OCF$_2$)$_s$—OC(Z)F—(CF$_2$)$_t$—, q, r, and s are separately independent and are integers of 0 or more and 200 or less, the sum of q, r and s is at least 1, the existing sequence of each repeating unit noted with q, r or s and bracketed with brackets is arbitrary in the formula; in is an integer of 1-16, t is 0 or 1, Z is a fluoride atom or trifluoromethyl;

X is a bivalent organic group, preferably X is $C_{1-6}$ alkylidene, —CH$_2$C$_6$H$_4$— or —CH$_2$C$_6$H$_4$— which has a substitutent on phenyl ring;

$Y^1$, $Y^2$ are separately independently $C_{1-6}$ alkylidene;

$Q^1$, $Q^2$ are separately independently alkoxy, hydroxyl or a group that can be hydrolyzed to hydroxyl group;

$R^1$, $R^2$ are separately independently $C_{1-6}$ alkyl or phenyl;

n is an integer of 1-3, preferably, n is 3.

Preferably, the acyl halogenation agent is (COCl)$_2$, SOCl$_2$, POCl$_3$, PCl$_5$ or SOBr$_2$.

Preferably, preparation of the starting raw material Rf—CH$_2$—O—X—COOH used in the forementioned reaction comprises:

Step 1: first reacting the compound of formula Rf—CH$_2$OH with a base in the presence of a solvent, and then making a nucleophilic substitution reaction with a compound of formula L-X-G, wherein, L is a leaving group or atom where a nucleophilic substitution reaction can occur, G is a group that can be hydrolyzed to carboxylic acid; X is a bivalent organic group, preferably X is $C_{1-6}$ alkylidene, —CH$_2$C$_6$H$_4$— or —CH$_2$C$_6$H$_4$— which has a substitutent on phenyl ring; obtaining an esteryl perfluorinated polyether compound of formula Rf—CH$_2$—O—X-G,

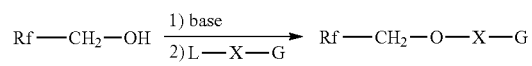

Step 2: hydrolyzing the compound of formula Rf—CH$_2$—O—X-G to obtain a carboxyl perfluorinated polyether compound of formula Rf—CH$_2$—O—X—COOH,

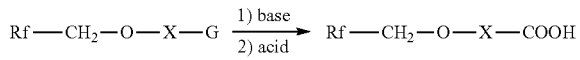

Wherein, Rf and X have the same meaning as those defined in the forementioned formula (3).

The base in step 1 is selected from inorganic base or organic base; inorganic base is preferably selected from at least one of LiOH, NaOH, KOH, K$_2$CO$_3$, Na$_2$CO$_3$, Cs$_2$CO$_3$, NaH, t-BuOK; organic base is preferably selected from at least one of DIPEA, DBU, 1,1,3,3-tetramethylguanidine.

Preferably, in the compound of formula L-X-G, L is chlorine atom, bromine atom, or iodine atom; G is ester group, nitrile group, amide group, or substituted amide group.

The solvent is fluorinated solvent, preferably hydrofluoroether or fluorinated hydrocarbon.

Preferably, the base in step 2 is selected from at least one of sodium hydroxide, potassium hydroxide, lithium hydroxide and cesium hydroxide.

Preferably, the acid in step 2 is selected from inorganic acid, and more preferably selected from at least one of hydrochloric acid, sulfuric acid, phosphoric acid or nitric acid.

Preferably, the aminosilane coupling agent is bis(alkoxy silane alkyl) amine.

Preferably, in the formula (3), Rf is CF$_3$(OC$_2$F$_4$)$_r$(OCF$_2$)$_s$OCF$_2$, wherein, r, s are separately independent and are integers of 0 or more and 200 or less, the sum of r, s is at least 1, the existing sequence of each repeating unit noted with r, s and bracketed with brackets is arbitrary in the formula; preferably, the sum of r, s is 20-100, more preferably, the sum of r, s 30-60;

X is C$_{1-6}$ alkylidene, —CH$_2$C$_6$H$_4$— or —CH$_2$C$_6$H$_4$— which has a substitutent on phenyl ring;

Y$^1$, Y$^2$ are separately independently C$_{1-6}$ alkylidene;

Q$^1$, Q$^2$ are separately independently alkoxy, hydroxyl or a group that can be hydrolyzed to hydroxyl group;

R$^1$, R$^2$ are separately independently C$_{1-6}$alkyl or phenyl.

The present invention also provides a surface treatment agent, which comprises the above perfluoropolyether group-containing silane compound as represented by formula (1), formula (2) or formula (3), the surface treatment agent further comprises a fluorinated solvent, the fluorinated solvent is hydrofluoroether.

Preferably, the surface treatment agent comprises 0.01-30 wt %, preferably 0.05-20 wt % or 10-20 wt % of the above perfluoropolyether group-containing silane compound.

The present invention also relates to an article having a coating formed by the above surface treatment agent, and the coating has a surface water contact angle of at least 110 degrees and a dynamic friction coefficient of not more than 0.05.

The article may be but not limited to display screen of optical component, smartphone, Tablet or computer.

The perfluoropolyether group-containing silane compound of the present invention has good hydrophobicity, lipophobicity, smoothness, steel velvet abrasion resistance and eraser abrasion resistance. In addition, the preparation process of the perfluoropolyether group-containing silane compound of the present invention reduces the difficulty of synthesis, simples the step process, and greatly reduces the production cost. This is mainly demonstrated in that: the used materials are all commercially available conventional products and are easy to be obtained; the reactions that perfluoropolyether was modified to give a new intermediate, and the reactions that the new intermediate is combined with silane coupling agent are all the conventional chemical reactions, the conditions of which are mild and easy to control; there are fewer steps required for product synthesis, simpler steps for separation and purification, and more advantageous production costs.

The surface treatment agent prepared by the perfluoropolyether compound of the present invention can be used for the surface of a substrate such as a glass, such that the substrate such as the glass treated by the surface treatment agent are excellent in anti-fouling, anti-fingerprint, scrape resistant and abrasion resistant performances.

DETAILED DESCRIPTION OF THE INVENTION

Figure 1:
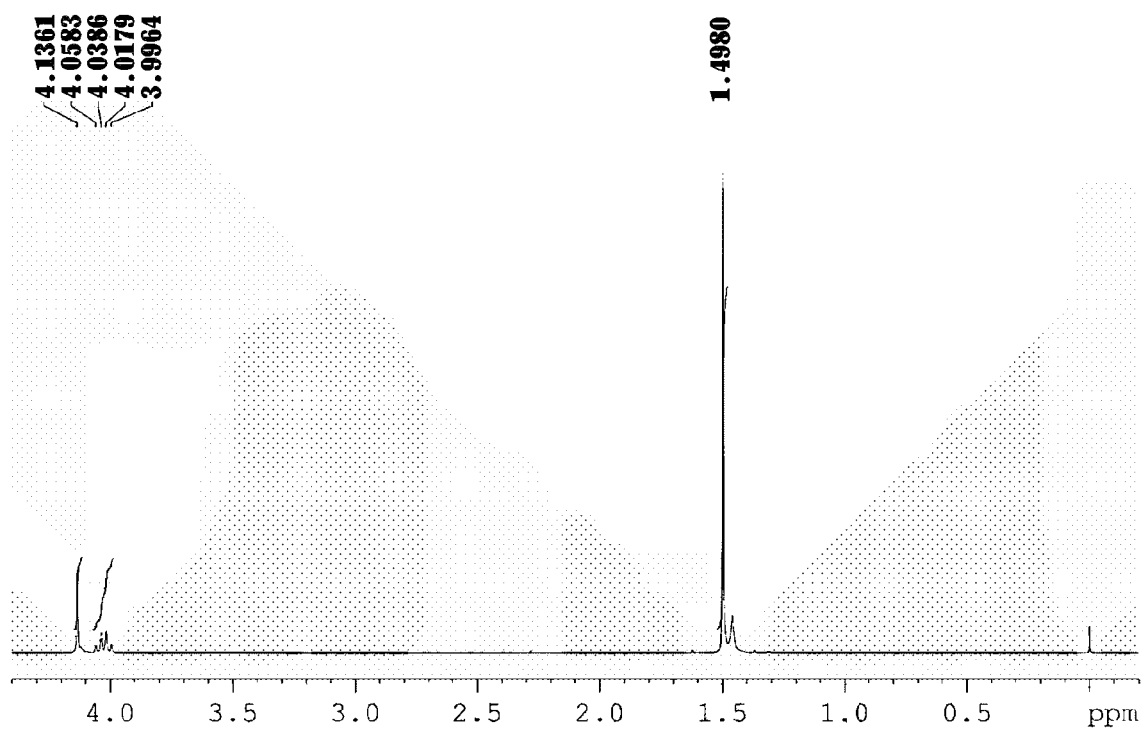
FIG. 1 is NMR spectrum of esteryl perfluoropolyether compounds (M1) in Synthesis Example 1.
Figure 2:
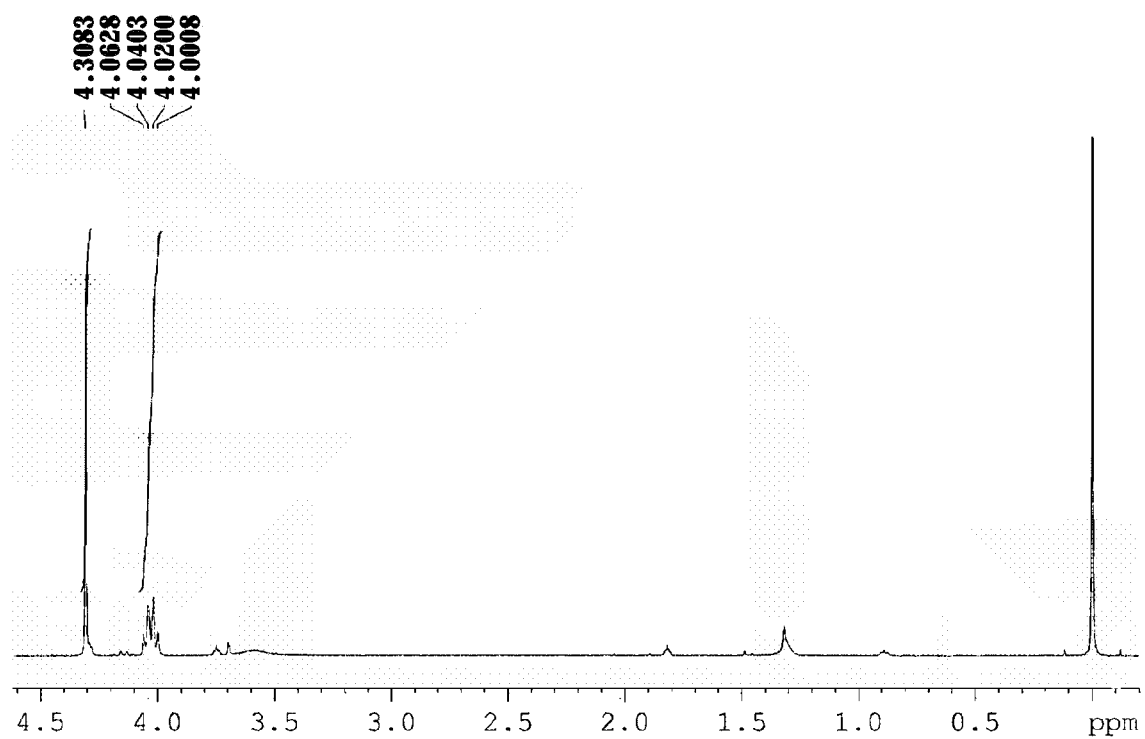
FIG. 2 is NMR spectrum of carboxyl perfluoropolyether compounds (M2) in Synthesis Example 1.
Figure 3:
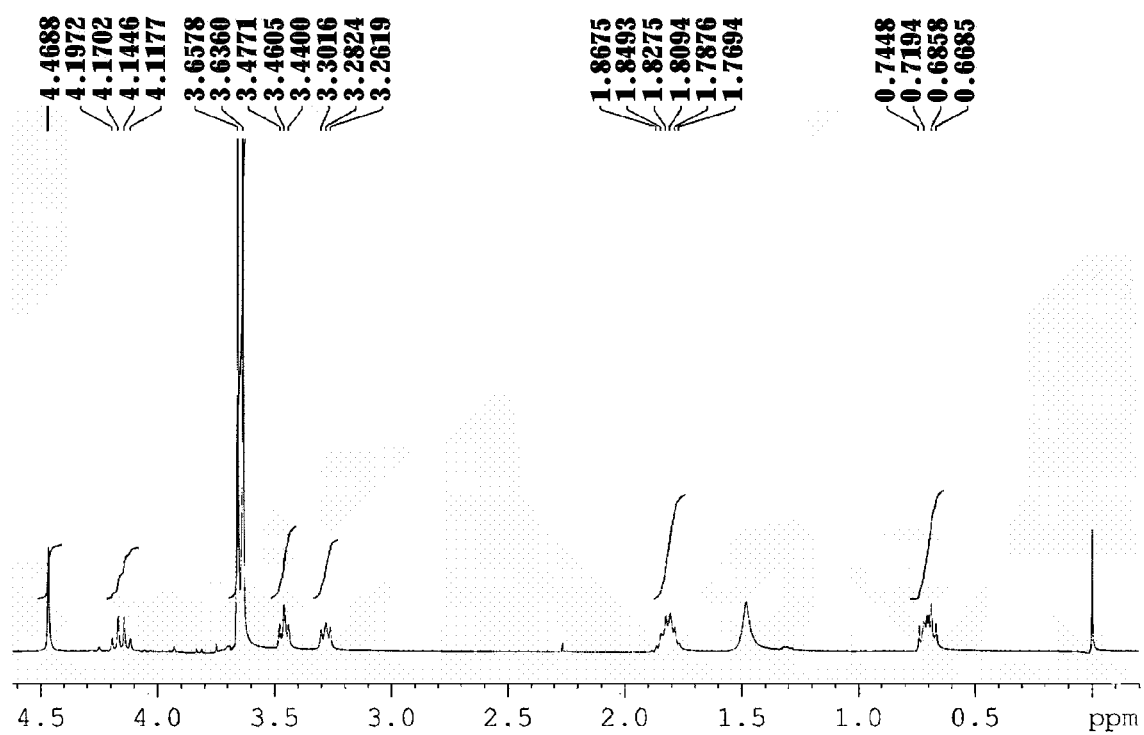
FIG. 3 is NMR spectrum of perfluoropolyether silane compounds (A1) in Synthesis Example 1.
Figure 4:
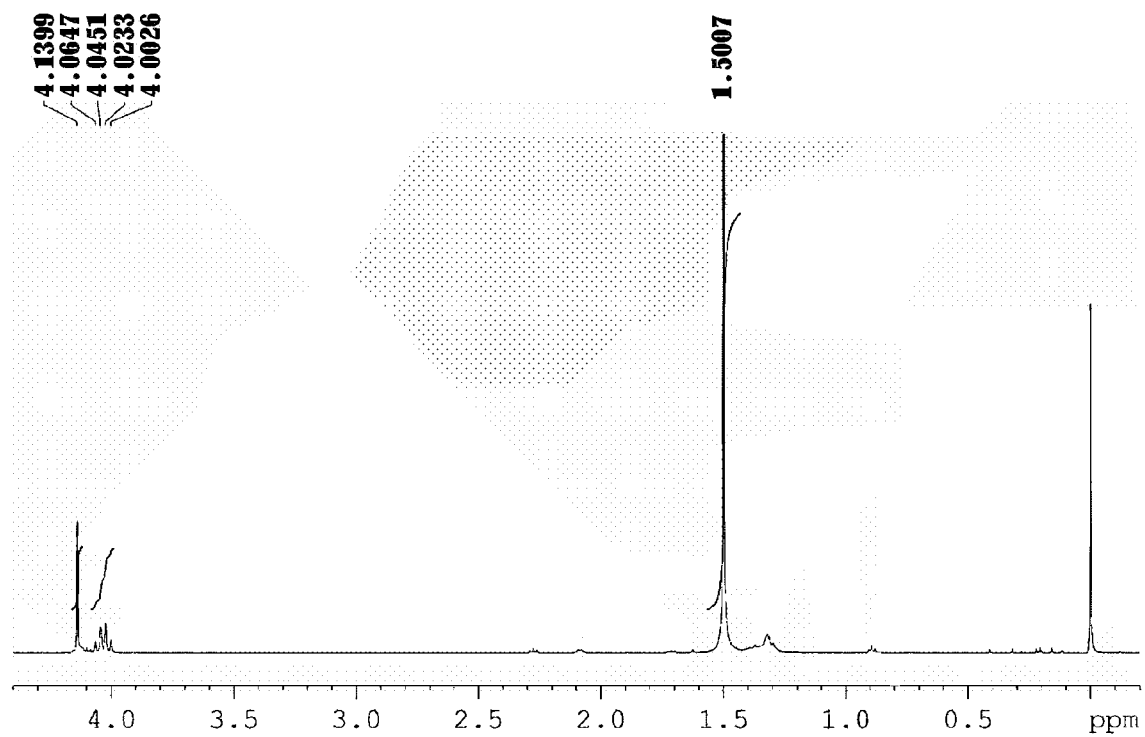
FIG. 4 is NMR spectrum of esteryl perfluoropolyether compounds (M3) in Synthesis Example 2.
Figure 5:
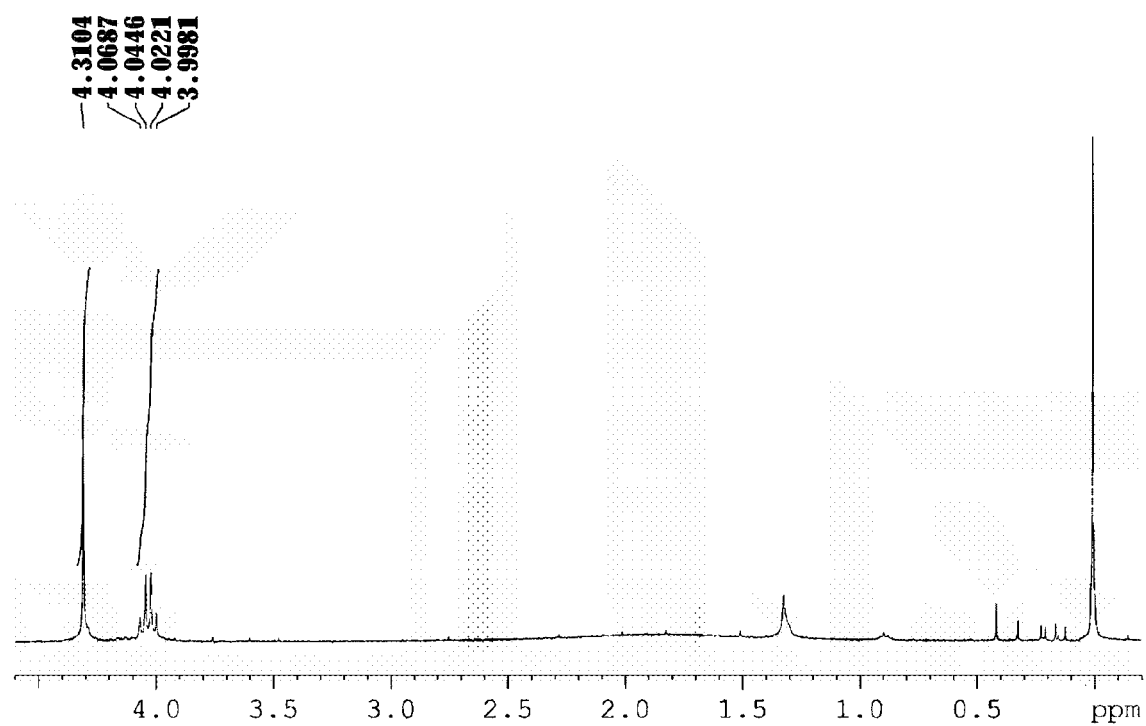
FIG. 5 is NMR spectrum of carboxyl perfluoropolyether compounds (M4) in Synthesis Example 2.
Figure 6:
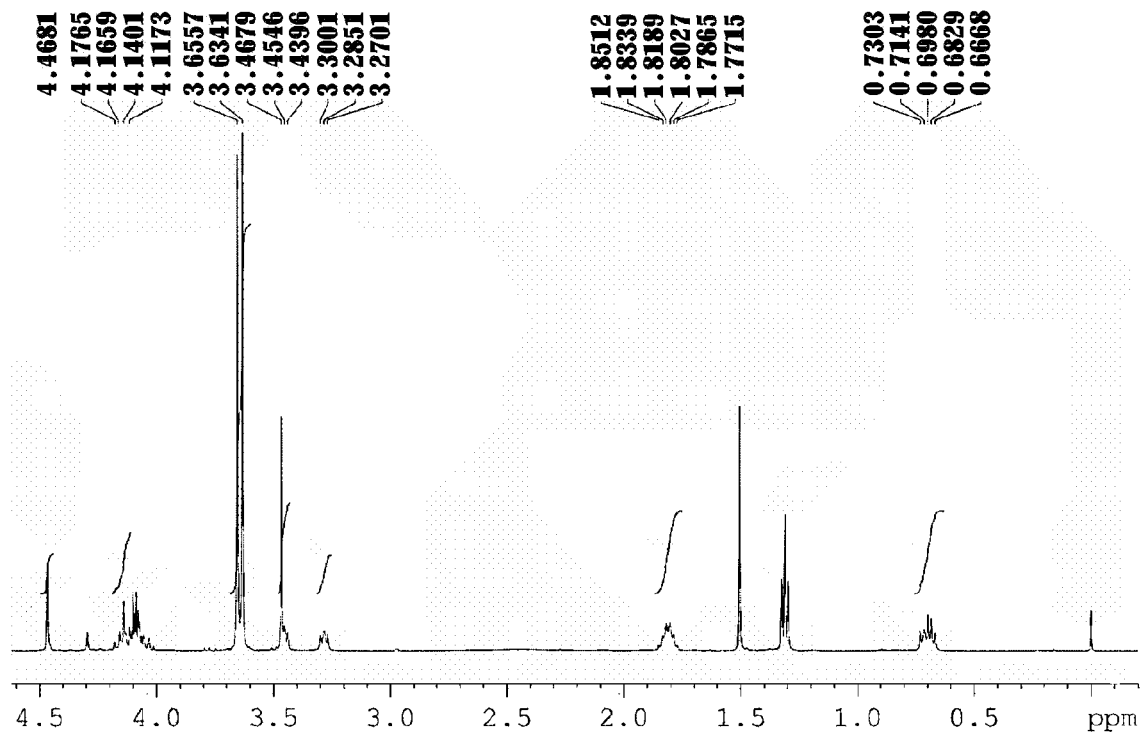
FIG. 6 is NMR spectrum of perfluoropolyether silane compounds (A2) in Synthesis Example 2.
Figure 7:
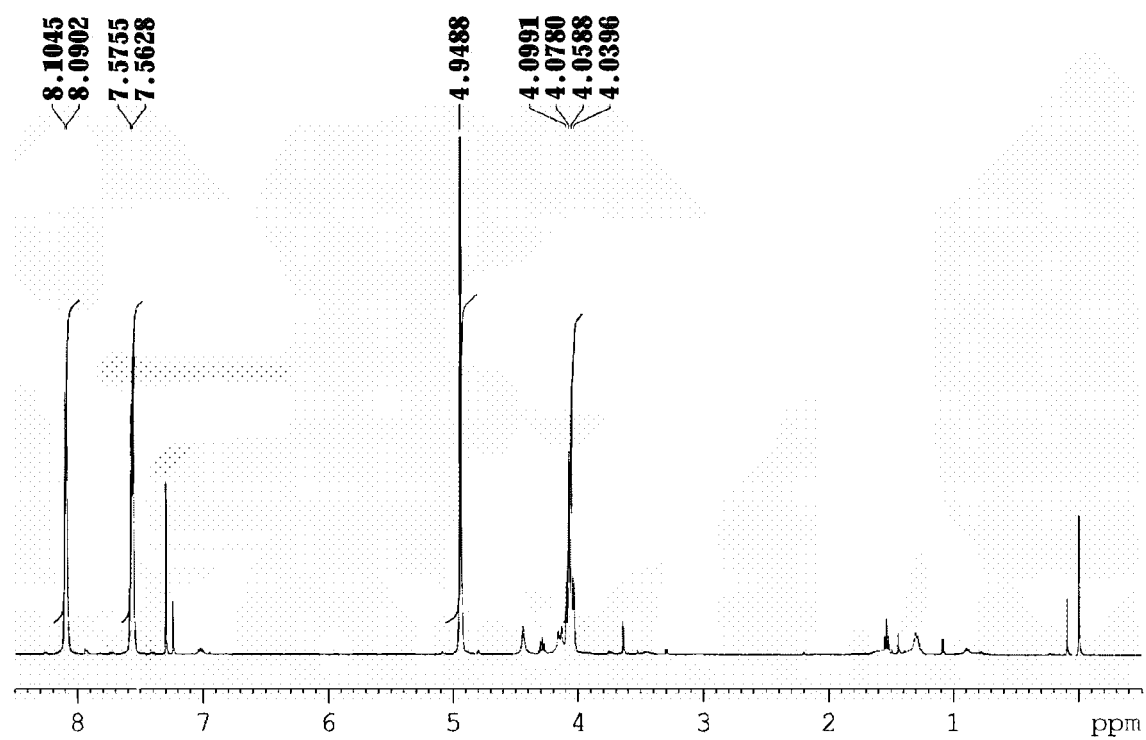
FIG. 7 is NMR spectrum of esteryl perfluoropolyether compounds (M6) in Synthesis Example 3.
Figure 8:
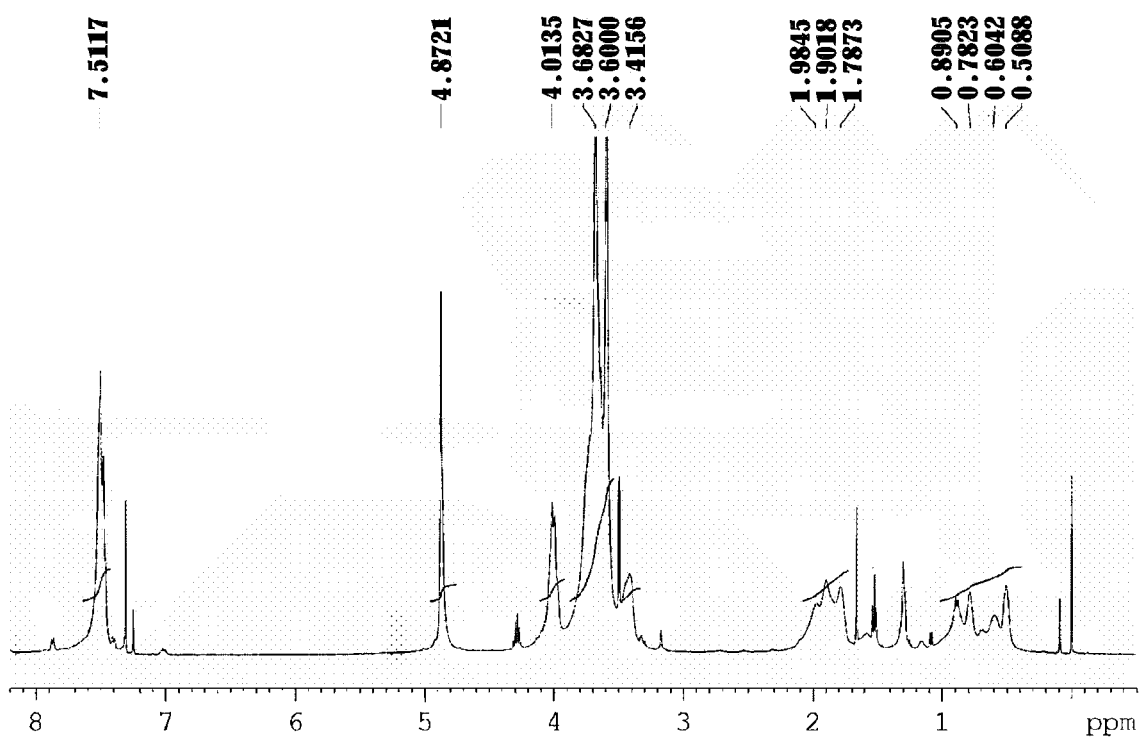
FIG. 8 is NMR spectrum of perfluoropolyether compounds (A3) in Synthesis Example 3.
Figure 9:
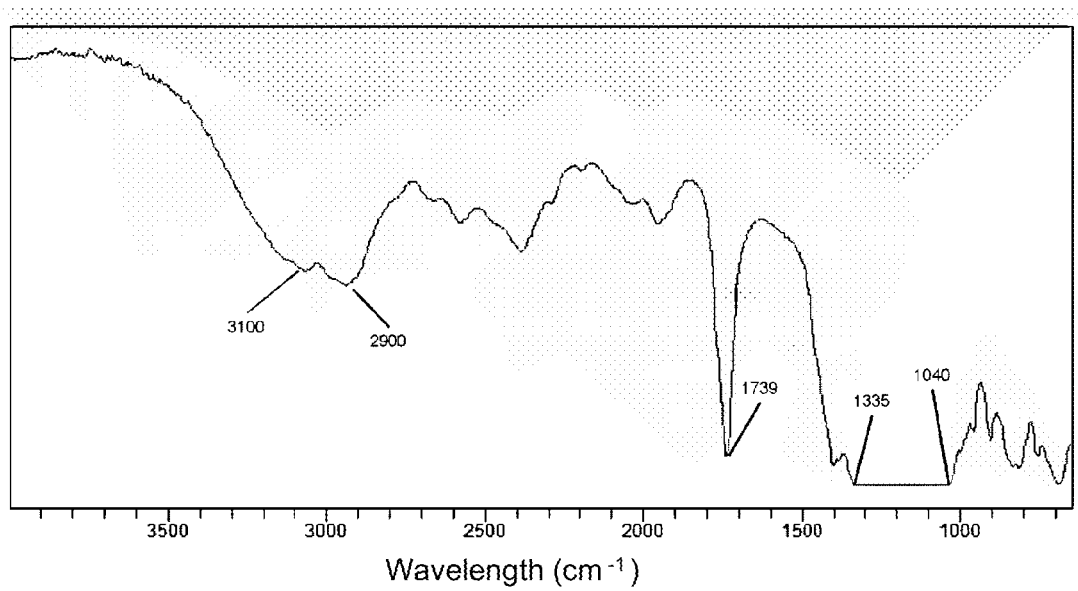
FIG. 9 is infrared spectrum of carboxyl perfluoropolyether compounds (M2) in Synthesis Example 3.

In sequence to make the purpose, technical solution and advantage of the present invention clearer, the technical solution in the examples of the present invention will be clearly and completely described below. It is obvious that the described examples are one portion of the Examples of the present invention, but not all the examples. Based on the examples of the present invention, all the other examples obtained without creative labor by one of ordinary skill in the art fall into the scope protected by the present invention.

Sufficiently detailed description is made below to each specific example of the present application, such that one of ordinary skill in the art having related knowledge and techniques in the art can carry out the technical solution of the present application. It should be understood that other examples can also be used, or that modifications or changes can be made to the examples of the present application.

Judging from the current market and industry requirements, the synthesis technology of existing commercially available products has higher difficulty, with many steps, long processes, or special material structures that are not easy to obtain, resulting in high production costs for its products. In view of these problems, this application uses a new synthesis path to obtain products with different structures, which reduces the synthesis difficulty, simples the step process and thus relatively reduces the production cost, while maintaining the comprehensive performance to meet the requirements. This is mainly demonstrated in that: (1) the materials used are commercially available conventional products and are easy to obtain; (2) the reactions that perfluoropolyether is modified to give a new intermediate, and the reactions that the new intermediate is combined with silane coupling agents, are conventional chemical reactions, and the conditions of which are mild and easy to control; (3) The synthesis of product requires fewer steps, and the separation and purification steps are relatively simple, so the production is more advantageous in cost.

For this, the present invention provides a perfluoropolyether group-containing silane compound represented by formula (1):

$$Rf—X^1—X^2—NQ_kT_{2-k} \qquad (1)$$

In the above formula, Rf is F—$(CF_2)_m$—$(OC_4F_8)_p$—$(OC_3F_6)_q$—$(OC_2F_4)_r$—$(OCF_2)_s$—OC(Z)F$(CF_2)_t$—, here, p, q, r and s p, q, r and s are separately independent and are integers of 0 or more and 200 or less, the sum of p, q, r and s is at least 1, the existing sequence and number of each repeating unit with p, q, r and s and bracketed with brackets are arbitrary in the formula; in and t are separately integers of 0 or more and 30 or less, Z is F or $CF_3$;

Rf may be the following formula (a) or (b):

$$CF_3—(OC_2F_4)_r—(OCF_2)_s—OCF_2— \qquad (a):$$

wherein, the sum of r and s is an integer of 10 or more and 200 or less;

$$F—(CF_2)_m—(OC_4F_8)_p—(OC_3F_6)_q—(OC_2F_4)_r—\\(OCF_2)_s—OC(Z)F(CF_2)_t; \qquad (b)$$

Wherein, in and t are separately independent, in is an integer of 1-16, t is an integer of 0-2, r and s are separately independent and are integers of 1 or more and 200 or less, the sum of p, q, r and s is 10 or more and 200 or less, the existing sequence and number of each repeating unit with p, q, r and s and bracketed with brackets are arbitrary in the formula.

In the forementioned formula (1), $X^1$ is a bivalent organic group; preferably $X^1$ is a group as shown below:—$R^4$—$X^3$—$X^4$—; wherein, $R^4$ is $C_{1-6}$ alkyl or substituted $C_{1-6}$ alkyl; $X^3$ is a group selected from —O—, —S—, ortho-, meta- or para-phenylene, ortho-, meta- or para-benzylidene, —C(O)O—, —CONR$^5$—, —O—CONR$^5$—, —NR$^5$—, —Si(R$^6$)$_2$—, —(Si(R$^6$)$_2$O)$_f$— Si(R$^6$)$_2$— and —(CH$_2$)$_g$—, $R^5$, when present at each time, is separately independent and is a hydrogen atom, phenyl or $C_{1-6}$ alkyl; $R^6$ is $C_{1-6}$ alkyl or substituted $C_{1-6}$ alkyl; $X^4$ is a bivalent group; f, when present at each time, is separately independent and is an integer of 1-100, g, when present at each time, is separately independent and is an integer of 1~20;

In the forementioned formula (1), $X^2$ is carbonyl (—CO—), sulfuryl (—SO—) or anhydride.

In the forementioned formula (1), T, when present at each time, is separately independent and is hydroxyl, hydrolysable group or hydrocarbon group; preferably, T, when present at each time, is separately independent, and is selected from hydroxyl, —O (R$^7$), $C_{1-12}$ alkyl, $C_{2-12}$ alkenyl, $C_{2-12}$ alkynyl and phenyl, $R^7$ is $C_{1-12}$ alkyl. More preferably, T, when present at each time, is separately independent, and is hydroxyl, or —O(R$^7$), $R^7$ is $C_{1-12}$ alkyl.

In the forementioned formula (1), Q, when present at each time, is separately independent and is —Y—SiR$^1_j$R$^2_{3-j}$, wherein, Y, when present at each time, is separately independent and is a bivalent organic group; $R^1$, when present at each time, is separately independent and is alkoxy, hydroxyl or a group that can be hydrolyzed to hydroxyl group; preferably, $R^1$ is —OR$^3$, wherein, $R^3$ is substituted or unsubstituted $C_{1-3}$ alkyl, preferably, $R^3$ is methyl; wherein, $R^2$, when present at each time, is separately independent and is $C_{1-22}$ alkyl, or Q'; wherein, Q' and Q have the same meanings; j is separately independent in each of Q and Q', being an integer selected from 0~3, the sum of j is 1 or more; k is separately independently 1 or 2, preferably, k is 2.

According to some preferred embodiments, the forementioned $X^4$ is a group as represented by —$(R^7)_a$—$(X^5)_b$—$R^8$—; wherein, $R^7$ is —$(CH_2)_c$—, ortho-, meta- or para-phenylene, or ortho-, meta- or para-benzylidene; $R^8$ is —$(CH_2)_d$—, ortho-, meta- or para-phenylene, or ortho-, meta- or para-benzylidene; $X^5$ is —$(X^6)_e$—; wherein, $X^6$, when present at each time, is separately independent, and is a group selected from —O—, —S—, ortho-, meta- or para-phenylene, ortho-, meta- or para-benzylidene, —C(O)O—, —CONR$^5$—, —O—CONR$^5$—, —Si(R$^6$)$_2$—, —(Si(R$^6$)$_2$O)$_f$— Si(R$^6$)$_2$— and —(CH$_2$)$_g$—; $R^5$, when present at each time, is separately independent, and is a hydrogen atom, phenyl or $C_{1-6}$ alkyl; $R^6$, when present at each time, is separately independent, and is phenyl or $C_{1-6}$ alkyl; f, when present at each time, is separately independent, and is an integer of 1~100; g, when present at each time, is separately independent, and is an integer of 1~20; c is an integer of 1~20; d is an integer of 1~20; e is an integer of 1~10; a is 0 or 1; b is 0 or 1.

According to some preferred embodiments, the perfluoropolyether group-containing silane compound as represented by the forementioned formula (1) has the number average molecule weight of 500~10,000, preferably 1000-8000, more preferably 3000-6000.

The present invention also provides a method for preparing a perfluoropolyether group-containing silane compound as represented by the forementioned formula (1), the method comprises reacting Rf—$X^1$—$X^2$—OH with an acyl halogenation agent and an aminosilane coupling agent to produce Rf—$X^1$—$X^2$—NQ$_k$T$_{2-k}$;

$$Rf—X^1—X^2—OH \text{ acyl halogenation agent+aminosilane coupling agent} \rightarrow Rf—X^1—X^2—NQ_kT_{2-k}$$

According to some preferred embodiments, the acyl halogenation agent is acyl halide, thionyl halide or phosphoryl halide, preferably acyl chloride, sulfuryl chloride, phosphonyl chloride, more preferably acyl chloride, most preferably oxaloyl chloride.

According to some preferred embodiments, the aminosilane coupling agent is HNQ$_k$T$_{2-k}$, wherein Q is —Y—SiR$^1_j$R$^2_{3-j}$, wherein, Y is a bivalent organic group; $R^1$ is alkoxy, hydroxyl or a group that can be hydrolyzed to hydroxyl group; preferably, $R^1$ is —OR$^3$, wherein, $R^3$ is substituted or unsubstituted $C_{1-3}$ alkyl, preferably, $R^3$ is methyl, ethyl, propyl or isopropyl; wherein, $R^2$ is $C_{1-22}$ alkyl, or Q'; wherein, Q' and Q has the same meaning; j is separately independent in each of Q and Q', being an integer selected from 0~3, the sum of j is 1 or more; k is separately independently 1 or 2, preferably, k is 2; T is hydroxyl, hydrolysable group or hydrocarbon group; preferably, T is selected from hydroxyl, —O(R$^7$), $C_{1-12}$ alkyl, $C_{2-12}$ alkenyl, $C_{2-12}$ alkynyl and phenyl, $R^7$ is $C_{1-12}$ alkyl; more preferably, T is hydroxyl, or —O(R$^7$), $R^7$ is $C_{1-12}$ alkyl.

According to some preferred embodiments, the present invention provides a perfluoropolyether group-containing silane compound as represented by formula (2), (2)

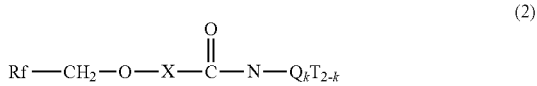

Wherein, Rf is

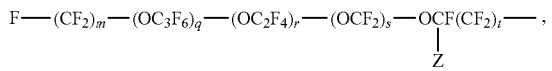

q, r and s are separately independent and are integers of 0 or more and 200 or less, the sum of q, r and s is at least 1, the existing sequence of each repeating unit noted with q, r or s and bracketed with brackets is arbitrary in the formula; in is an integer of 1-16, t is 0 or 1, Z is a fluoride atom or trifluoromethyl;

X is a bivalent organic group;

T, when present at each time, is separately independent and is hydroxyl, hydrolysable group or hydrocarbon group;

Q, when present at each time, is separately independent and is —Y—SiR$^1_j$R$^2_{3-j}$;

Y, when present at each time, is separately independent and is a bivalent organic group;

R$^1$, when present at each time, is separately independent and is alkoxy, hydroxyl or a group that can be hydrolyzed to hydroxyl group;

R$^2$, when present at each time, is separately independent and is C$_{1-22}$ alkyl or Q', Q' and Q have the same meaning;

j is separately independent in each of Q and Q', and is an integer selected from 0~3, the sum of j is 1 or more;

k is separately independent, and is 1 or 2.

According to more preferred embodiment, in the forementioned formula (2), k is 2.

According to some preferred embodiments, in the forementioned formula (2), X is a group represented by —(R$^3$)$_a$—(X$^1$)$_b$—R$^4$—, wherein, R$^3$ is —(CH$_2$)$_c$—, ortho-, meta- or para-phenylene, or ortho-, meta- or para-benzylidene; R$^4$ is —(CH$_2$)d-, ortho-, meta- or para-phenylene, or ortho-, meta- or para-benzylidene; X$^1$ is —(X$^2$)$_e$—, wherein X$^2$, when present at each time, is separately independent, and is a group selected from —O—, —S—, ortho-, meta- or para-phenylene, ortho-, meta- or para-benzylidene, —C(O)O—, —CONR$^5$—, —O—CONR$^5$—, —NR$^5$—, —Si(R$^6$)$_2$—, —(Si(R$^6$)$_2$O)$_f$—Si(R$^6$)$_2$— and —(CH$_2$)$_g$—, wherein R$^5$, when present at each time, is separately independent, and is a hydrogen atom, phenyl or C$_{1-6}$ alkyl; R$^6$, when present at each time, is separately independent, and is phenyl or C$_{1-6}$ alkyl; f, when present at each time, is separately independent, and is an integer of 1~100; g, when present at each time, is separately independent, and is an integer of 1~20; c is an integer of 1~20; d is an integer of 1~20; e is an integer of 1~10; a is 0 or 1; b is 0 or 1.

According to some preferred embodiments, in the forementioned formula (2), X is C$_{1-20}$ alkylidene, —R$^3$—X$^3$—R$^4$— or —X$^4$—R$^4$—, wherein, X$^3$ is —O—, —S—, —C(O)O—, —CONR$^5$—, —O—CONR$^5$—, —Si(R$^6$)$_2$—, —(Si(R$^6$)$_2$O)$_f$—Si(R$^6$)$_2$—, —O—(CH$_2$)$_h$—(Si(R$^6$)$_2$O)$_f$—Si(R$^6$)$_2$—, —CONR$^5$—(CH$_2$)$_h$—(Si(R$^6$)$_2$O)$_f$—Si(R$^6$)$_2$—, —CONR$^5$—(CH$_2$)$_h$—N(R$^5$)— or —CONR$^5$-(ortho-, meta- or para-phenylene)-Si(R$^6$)$_2$—; X$^4$ is —S—, —C(O)O—, —CONR$^5$—, —O—CONR$^5$—, —O—(CH$_2$)$_h$—(Si(R$^6$)$_2$O)$_f$—Si(R$^6$)$_2$—, —CONR$^5$—(CH$_2$)$_h$—N(R$^5$)— or —CONR$^5$-(ortho-, meta- or para-phenylene)-Si(R$^6$)$_2$—; wherein R$^3$ is —(CH$_2$)$_c$—, ortho-, meta- or para-phenylene, or ortho-, meta- or para-benzylidene; R$^4$ is —(CH$_2$)$_d$-ortho-, meta- or para-phenylene, or ortho-, meta- or para-benzylidene; R$^5$ is a hydrogen atom, phenyl or C$_{1-6}$ alkyl, R$^6$ is phenyl or C$_{1-6}$ alkyl; c is an integer of 1~20; d is an integer of 1~20; f is an integer of 1~100; h is an integer of 1~20.

According to some preferred embodiments, in the forementioned formula (2), R$^3$ is —(CH$_2$)$_c$—, R$^4$ is —(CH$_2$)$_d$—, wherein, c is an integer of 1~20; d is an integer of 1~20.

According to some preferred embodiments, in the forementioned formula (2), X is C$_{1-20}$ alkylidene, —(CH$_2$)$_c$—O—(CH$_2$)$_d$—, —(CH$_2$)$_c$—(Si(R$^6$)$_2$O)$_f$—Si(R$^6$)$_2$—(CH$_2$)$_d$—, —(CH$_2$)$_c$—O—(CH$_2$)$_h$—(Si(R$^6$)$_2$O)$_f$—Si(R$^6$)$_2$—(CH$_2$)$_d$—, wherein, R$^6$ is phenyl or C$_{1-6}$ alkyl; c is an integer of 1~20; d is an integer of 1~20; f is an integer of 1~100; h is an integer of 1~20.

According to some preferred embodiments, in the forementioned formula (2), X is selected from the following groups: —CH$_2$—, —(CH$_2$)$_2$—, —(CH$_2$)$_3$—, —(CH$_2$)$_4$—, —(CH$_2$)$_6$—, —CH$_2$C$_6$H$_4$—, —CH$_2$OCH$_2$—, —CH$_2$O(CH$_2$)$_2$—, —CH$_2$O(CH$_2$)$_3$—, —CH$_2$O(CH$_2$)$_6$—, —CH$_2$C$_6$H$_4$—OCH$_2$—, —CONH—(CH$_2$)$_3$—, —CON(CH$_3$)—(CH$_2$)$_3$—, —CON(Ph)-(CH$_2$)$_3$—, Ph is phenyl, —CON(CH$_3$)—(CH$_2$)$_6$—, —CON(Ph)-(CH$_2$)$_6$—, Ph is phenyl, —CONH—(CH$_2$)$_2$NH(CH$_2$)$_3$—, —CONH—(CH$_2$)$_6$NH(CH$_2$)$_3$—, —CH$_2$O—CONH—(CH$_2$)$_3$—, —CH$_2$O—CONH—(CH$_2$)$_6$—, —C(O)O—(CH$_2$)$_3$—, —C(O)O—(CH$_2$)$_6$—, —S—(CH$_2$)$_3$—, —(CH$_2$)$_2$S(CH$_2$)$_3$—, —CH$_2$O—(CH$_2$)$_3$Si(CH$_3$)$_2$OSi(CH$_3$)$_2$(CH$_2$)$_2$—, —CH$_2$O—(CH$_2$)$_3$Si(CH$_3$)$_2$OSi(CH$_3$)$_2$OSi(CH$_3$)$_2$(CH$_2$)$_2$—, —CH$_2$O—(CH$_2$)$_3$Si(CH$_3$)$_2$O(Si(CH$_3$)$_2$O)$_2$Si(CH$_3$)$_2$(CH$_2$)$_2$—.

According to some preferred embodiments, in the forementioned formula (2), T, when present at each time, is separately independent and is selected from hydroxyl, —O (R$^7$), C$_{1-12}$ alkyl, C$_{2-12}$ alkenyl, C$_{2-12}$ alkynyl and phenyl, R$^7$ is C$_{1-12}$ alkyl; more preferably, T, when present at each time, is separately independent and is hydroxyl, or —O (R$^7$), R$^7$ is C$_{1-12}$ alkyl.

According to some preferred embodiments, in —Y—SiR$^1_j$R$^2_{3-j}$ of Q, j is 3.

According to some preferred embodiments, the perfluoropolyether group-containing silane compound represented by the formula (2) has the number average molecule weight of 500~10,000, preferably 1000-8000, more preferably 3000-6000.

The present invention also provides a method for preparing a perfluoropolyether group-containing silane compound represented by the forementioned formula (2), the method comprises:

reacting and converting a compound of formula Rf—CH$_2$—O—X—COOH with an acyl halogenation agent and an aminosilane coupling agent to obtain a perfluoropolyether group-containing silane compound of formula (2),

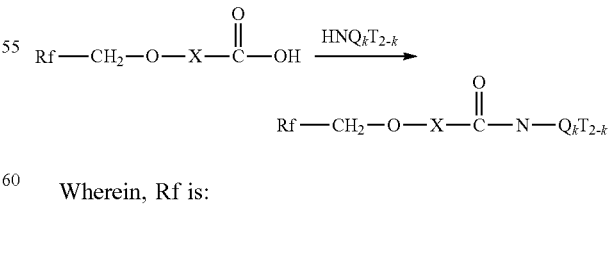

Wherein, Rf is:

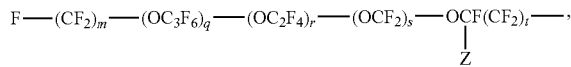

q, r and s are separately independent and are integers of 0 or more and 200 or less, the sum of p, q, r and s is at least 1, the existing sequence of each repeating unit noted with q, r or s and bracketed with brackets is arbitrary in the formula; in is an integer of 1-6, t is 0 or 1, Z is a fluoride atom or trifluoromethyl;

X is a bivalent organic group;

T, when present at each time, is separately independent and is hydroxyl, hydrolysable group or hydrocarbon group;

Q, when present at each time, is separately independent and is —Y—SiR$^1_j$R$^2_{3-j}$;

Y, when present at each time, is separately independent and is a bivalent organic group;

R$^1$, when present at each time, is separately independent and is alkoxy, hydroxyl or a group that can be hydrolyzed to hydroxyl group;

R$^2$, when present at each time, is separately independent and is C$_{1-22}$ alkyl or Q', Q' and Q have the same meaning;

j is separately independent in each of Q and Q', and is an integer selected from 0~3, the sum of j is 1 or more;

k is separately independent, and is 1 or 2.

According to some preferred embodiments, the acyl halogenation agent is acyl halide, preferably acyl chloride, and more preferably oxalyl chloride.

According to some preferred embodiments, the aminosilane coupling agent is HNQ$_k$T$_{2-k}$, wherein the meanings of Q, T, k are the same as those defined in the forementioned formula (2).

According to some preferred embodiments, preparation process of Rf—CH$_2$—O—X—COOH comprises:

Step 1: first reacting the compound of formula Rf—CH$_2$OH with a base in the presence of a solvent, and then making nucleophilic substitution reaction with a compound of formula L-X-G, obtaining a compound of formula Rf—CH$_2$—O—X-G, wherein in the formula L-X-G, L is a leaving group where a nucleophilic substitution reaction can occur, X is a bivalent organic group, G is a group that can be hydrolyzed to carboxylic acid,

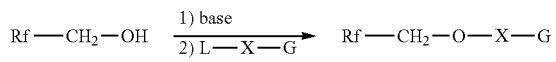

Step 2: chemically converting the compound of formula Rf—CH$_2$—O—X-G to obtain a compound of formula Rf—CH$_2$—O—X—COOH,

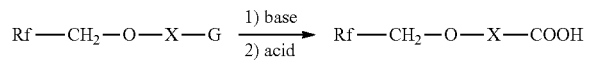

According to some preferred embodiments, the base in the forementioned step 1 is selected from inorganic base or organic base; inorganic base is preferably selected from at least one of LiOH, NaOH, KOH, K$_2$CO$_3$, Na$_2$CO$_3$, Cs$_2$CO$_3$, NaH, t-BuOK; organic base is preferably selected from at least one of DIPEA, DBU, 1,1,3,3-tetramethylguanidine. More preferably, the base is selected from at least one of sodium hydroxide, potassium hydroxide, lithium hydroxide, cesium hydroxide, sodium carbonate, potassium carbonate and cesium carbonate.

According to some preferred embodiments, in the compound of formula L-X-G of the forementioned step 1, L is selected from: chlorine atom, bromine atom, iodine atom, or other group(s) that can undergo nucleophilic substitution reaction.

According to some preferred embodiments, in the compound of formula L-X-G of the forementioned step 1, G is selected from: a group(s) of ester group, nitrile group, amide group, or substituted amide group.

According to some preferred embodiments, the base in step 2 is selected from at least one of sodium hydroxide, potassium hydroxide, lithium hydroxide and cesium hydroxide.

According to some preferred embodiments, the acid in step 2 is selected from an inorganic acid such as hydrochloric acid, sulfuric acid, phosphoric acid or nitric acid.

According to some preferred embodiments, the present invention provides a perfluoropolyether group-containing silane compound represented by formula (3),

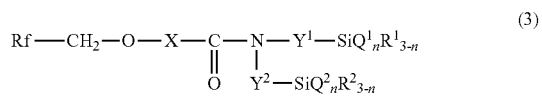

wherein, wherein, Rf is F—(CF$_2$)$_m$—(OC$_3$F$_6$)$_q$—(OC$_2$F$_4$)$_r$—(OCF$_2$)$_s$—OC(Z)F—(CF$_2$)$_t$—, q, r, and s are separately independent and are integers of 0 or more and 200 or less, the sum of q, r and s is at least 1, the existing sequence of each repeating unit noted with q, r or s and bracketed with brackets is arbitrary in the formula; in is an integer of 1-16, t is 0 or 1, Z is a fluoride atom or trifluoromethyl;

X is a bivalent organic group, preferably X is C$_{1-6}$ alkylidene, —CH$_2$C$_6$H$_4$— or —CH$_2$C$_6$H$_4$— which has a substitutent on phenyl ring;

Y$^1$, Y$^2$ are separately independently C$_{1-6}$ alkylidene;

Q$^1$, Q$^2$ are separately independently alkoxy, hydroxyl or a group that can be hydrolyzed to hydroxyl group;

R$^1$, R$^2$ are separately independently C$_{1-6}$ alkyl or phenyl;

n is an integer of 1-3, preferably, n is 3.

According to more preferred embodiment, in the formula (3), Rf is CF$_3$(OC$_2$F$_4$)$_r$(OCF$_2$)$_s$OCF$_2$, wherein, r, s are separately independent and are integers of 0 or more and 200 or less, the sum of r, s is at least 1, the existing sequence of each repeating unit noted with r, s and bracketed with brackets is arbitrary in the formula; preferably, the sum of r, s is at least 10, more preferably 10-100, and further preferably 20-80, and most preferably 30-60;

X is C$_{1-6}$ alkylidene, —CH$_2$C$_6$H$_4$— or —CH$_2$C$_6$H$_4$— which has a substitutent on phenyl ring;

Y$^1$, Y$^2$ are separately independently C$_{1-6}$ alkylidene;

Q$^1$, Q$^2$ are separately independently alkoxy, hydroxyl or a group that can be hydrolyzed to hydroxyl group;

R$^1$, R$^2$ are separately independently C$_{1-6}$ alkyl or phenyl.

According to some preferred embodiments, the forementioned r, s are separately independently integers of 0 or more and 100 or less, or integers of 10-50, the sum of r, s is at least 10, or at least 20.

According to some preferred embodiments, in the forementioned formula (3), X is —CH$_2$— or —CH(CH$_3$)—.

According to some preferred embodiments, in the forementioned formula (3), Y$^1$ and Y$^2$ are separately —(CH$_2$)$_3$—.

According to some preferred embodiments, in the forementioned formula (3), Q$^1$, Q$^2$ are separately independently C$_{1-6}$ alkoxy.

According to some preferred embodiments, in the forementioned formula (3), $Q^1$, $Q^2$ are separately —$OCH_3$, —$OC_2H_5$, —$OC_3H_7$, —$OC(CH_3)_2$.

According to some preferred embodiments, in the forementioned formula (3), n is 3.

According to some preferred embodiments, the perfluoropolyether group-containing silane compound represented by the forementioned formula (3) has the number average molecule weight of 500~10,000, preferably 1000-8000, more preferably 3000-6000.

According to some preferred embodiments, the present invention provides a method for preparing a perfluoropolyether group-containing silane compound represented by the forementioned formula (3),

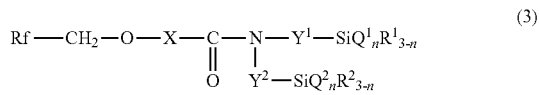

(3)

The method comprises: reacting Rf—$CH_2$—O—X—COOH with acyl halogenation agent and aminosilane coupling agent,

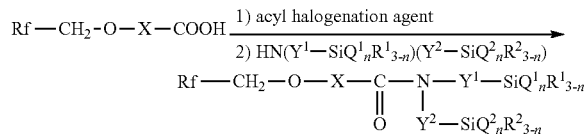

wherein, Rf is F—$(CF_2)_m$—$(OC_3F_6)_q$—$(OC_2F_4)_r$—$(OCF_2)_s$—$OC(Z)F$—$(CF_2)_t$—, q, r, and s are separately independent and are integers of 0 or more and 200 or less, the sum of q, r and s is at least 1, the existing sequence of each repeating unit noted with q, r or s and bracketed with brackets is arbitrary in the formula; in is an integer of 1-16, t is 0 or 1, Z is a fluoride atom or trifluoromethyl; or Rf is $CF_3(OCF_2CF_2)_r(OCF_2)_sOCF_2$, wherein, r, s are separately independently integers of 0 or more and 200 or less, the sum of r, s is at least 1, the existing sequence of each repeating unit noted with r, s and bracketed with brackets is arbitrary in the formula; preferably, the sum of r, s is at least 10, more preferably 10-100, further preferably 20-80, most preferably 30-60;

X is a bivalent organic group, preferably X is $C_{1-6}$ alkylidene, —$CH_2C_6H_4$— or —$CH_2C_6H_4$— which has a substitutent on phenyl ring;

$Y^1$, $Y^2$ are separately independently $C_{1-6}$ alkylidene;

$Q^1$, $Q^2$ are separately independently alkoxy, hydroxyl or a group that can be hydrolyzed to hydroxyl group;

$R^1$, $R^2$ are separately independently $C_{1-6}$ alkyl or phenyl;

n is an integer of 1-3, preferably, n is 3.

According to some preferred embodiments, the used acyl halogenation agent is not particularly limited, and for the above reaction, acyl halide, particularly acyl chloride, and more particularly oxalyl chloride may be preferably used.

According to some embodiments, preparation process of Rf—$CH_2$—O—X—COOH comprises:

Step 1: first reacting the compound of formula Rf—$CH_2OH$ with a base in the presence of a solvent, and then making a nucleophilic substitution reaction with a compound of formula L-X-G, wherein, L is a leaving group where a nucleophilic substitution reaction can occur, G is a group that can be hydrolyzed to carboxyl; X is a bivalent organic group, obtaining an esteryl perfluorinated polyether compound of formula Rf—$CH_2$—O—X-G,

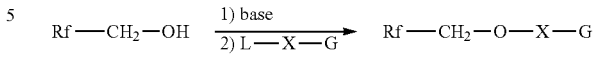

Step 2: hydrolyzing the compound of formula Rf—$CH_2$—O—X-G to obtain a carboxyl perfluorinated polyether compound of formula Rf—$CH_2$—O—X—COOH,

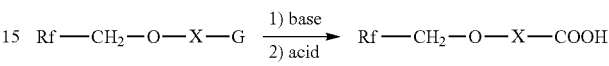

Wherein, Rf, X, G have the same meanings as those defined in the forementioned formula (3).

According to some preferred embodiments, the base in step 1 is selected from inorganic base or organic base; the inorganic base is preferably selected from at least one of LiOH, NaOH, KOH, $K_2CO_3$, $Na_2CO_3$, $Cs_2CO_3$, NaH, t-BuOK; the organic base is preferably selected from at least one of DIPEA, DBU, 1,1,3,3-tetramethylguanidine. More preferably, the base is selected from: at least one of sodium hydroxide, potassium hydroxide, lithium hydroxide, cesium hydroxide, sodium carbonate, potassium carbonate and cesium carbonate.

According to some preferred embodiments, in the compound of the forementioned formula L-X-G, L is chlorine atom, bromine atom, or iodine atom.

According to some preferred embodiments, in the compound of the forementioned formula L-X-G, X is $C_{1-20}$ alkylidene, more preferably $C_{1-6}$ alkylidene, —$CH_2C_6H_4$— or —$CH_2C_6H_4$— which has a substitutent on phenyl ring.

According to some preferred embodiments, in the compound of the forementioned formula L-X-G, G is ester group, nitrile group, amide group, or substituted amide group. Further, the examples of the ester may be methyl ester, ethyl ester, propyl ester, isopropyl ester, benzyl ester, etc. The examples of the amides may be N-substituted amide or N,N-disubstituted amide.

According to some preferred embodiments, the examples of the compound of L-X-G comprise but not limited to:

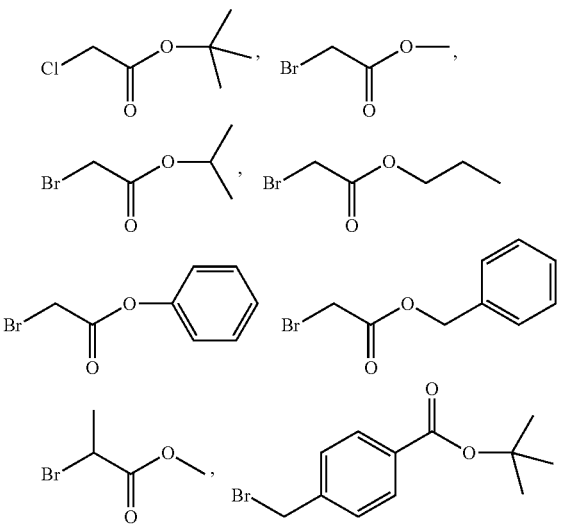

-continued

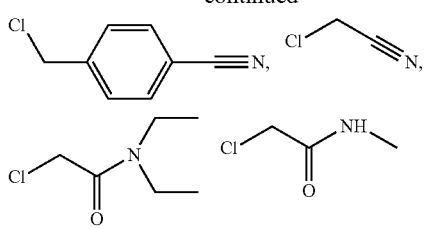

According to some preferred embodiments, the base in the forementioned step 2 is selected from at least one of sodium hydroxide, potassium hydroxide, lithium hydroxide and cesium hydroxide.

According to some preferred embodiments, the acid in the forementioned step 2 is selected from an inorganic acid, and the examples of the inorganic acid may comprise hydrochloric acid, sulfuric acid, phosphoric acid or nitric acid.

According to some preferred embodiments, the acylating agent is acyl halide, preferably acyl chloride, and more preferably oxalyl chloride.

According to some preferred embodiments, the aminosilane coupling agent is preferably bis(alkoxy silane alkyl) amine, more preferably bis(alkoxy silane alkyl) amine.

According to one more preferred embodiment of the present invention, a method for preparing a perfluoropolyether group-containing silane compound comprises the following steps:

Step 1: first reacting a compound of formula Rf—CH$_2$OH with potassium hydroxide at room temperature, and then making a nucleophilic substitution reaction with the compound of formula BrCH$_2$COOC$_4$H$_9$ at normal or heated (preferably 25-75° C.) temperature, obtaining an esteryl perfluorinated polyether compound of formula Rf—CH$_2$OCH$_2$COOC$_4$H$_9$,

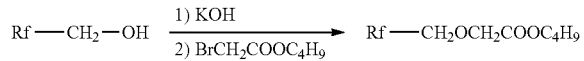

Rf is CF$_3$(OCF$_2$CF$_2$)$_r$(OCF$_2$)$_s$OCF$_2$—, r+s is 35-85, which has a number average molecule weight of 3000-8000;

Step 2: reacting the esteryl perfluorinated polyether compound of formula Rf—CH$_2$—OCH$_2$ COOC$_4$H$_9$ with a base to be hydrolyzed, adding hydrochloric acid to adjust acidity, separating and obtaining a carboxyl perfluorinated polyether compound of formula Rf—CH$_2$—O—CH$_2$COOH,

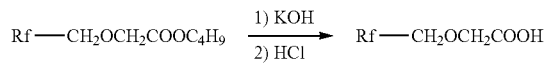

Step 3: reacting a carboxyl perfluorinated polyether compound of formula Rf—CH$_2$—O—CH$_2$COOH with oxalyl chloride at a temperature of 25-50° C., then reacting and converting it with bis(trimethylsilane propyl) amine at room temperature to obtain a perfluoropolyether silane compound of formula Rf—CH$_2$—O—CH$_2$CON[CH$_2$CH$_2$CH$_2$Si (OCH$_3$)$_3$]$_2$.

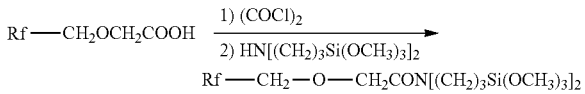

In the preparation process of the present invention, there is no limitation to the solvent used, as long as it is a solvent that can dissolve perfluorinated polyether alcohol, esteryl polyfluorinated polyether compound, carboxyl polyfluorinated polyether compound and the like under the condition of normal temperature or heating. It is preferably a fluorinated solvent, such as hydrofluoroether, fluorinated hydrocarbon, etc., and more preferably nonafluorobutyl ethyl ether, nonafluorobutyl methyl ether, perfluorohexane, m-trifluorotoluene, etc.

The preparation process of the present invention may be conducted under the condition of normal temperature or heating. It is preferred that the nucleophilic substitution reaction of perfluorinated polyether alcohol in step 1 may be conducted at 25-75° C., and it is preferred that the acyl halogenation reaction in step 3 may be conducted at 25-50° C.

As described above, in the present invention, an esteryl perfluorinated polyether compound of formula Rf—CH$_2$—O—X-G is obtained by making a nucleophilic substitution reaction with a compound of formula Rf—CH$_2$OH and a compound of formula L-X-G, wherein, L is a leaving group where a nucleophilic substitution reaction can occur, G is a group that can be hydrolyzed to carboxyl, X is a bivalent organic group, and then a completely new intermediate carboxyl perfluorinated polyether compound of formula Rf—CH$_2$—O—X—COOH is obtained by hydrolyzation. Since the perfluorinated polyether group is connected to the carboxyl group through the spacing group X, the subsequent further reactions of the carboxyl group become easy to be realized, such as reaction with the aminosilane coupling agent can obtain the perfluorinated polyether group-containing amino silane compound of the invention. The intermediate of formula Rf—CH$_2$—O—X—COOH can be used as a starting material to easily perform further follow-up reactions of carboxyl groups, thereby obtaining a variety of derivative compounds containing perfluorinated polyetheryl and carbonyl group(s). For example, the carboxyl group can react with the acyl halogenation agent to form acylhalide, condense with the carboxylate to form anhydride, condense with alcohols to form esters, react with amines to form amides, and primary amides can also be dehydrated so as to be prepared into nitrile.

Since the perfluoropolyether group-containing silane compound obtained by the present invention is a specific perfluoropolyether group-containing amino siloxane compound, it is suitable for use as a surface treatment agent. The surface treatment agent may comprise a mixture of one or more of the perfluoropolyether group-containing silane compounds of the present invention and a liquid medium such as an organic solvent. The organic solvent may be a variety of solvents which capable of dissolving the compound under the condition that the solvent does not react with the compound of the invention. Examples of the organic solvents include fluorinated solvents, such as fluorinated alkanes, fluorinated halogenated hydrocarbons, fluorinated aromatic hydrocarbons, such as hydrofluoroether, etc., and may also be a combination of different solvents. The concentration of the perfluoropolyether group-containing silane compound of the present invention in the surface treatment agent can be adjusted as needed, usually 0.01-30 wt %, preferably 0.05-20 wt %, and more preferably 10-20 wt %. According to the different coating methods used, different concentrations are selected, for example, high concentrations are suitable for dry coating and low concentrations are suitable for wet coating. It can also be prepared into high concentrations and diluted when used according to the needs of the coating method.

When the surface treatment agent of the invention is used to treat the surface, even if the resulting layer is only a few nanometers thick, a surface having a water contact angle of 110 degrees or more, preferably 115 degrees or more, and a dynamic friction coefficient of less than 0.05 can be formed, as shown in the following examples.

There is no particular limit to the substrate which is treated by the surface treatment agent of the present invention to form a surface treatment layer. Examples thereof can include optical components, cell phones, tablet computers, etc., including inorganic substrates such as glass plates, glass plates containing inorganic layers, and ceramics; and organic substrates such as transparent plastic substrates and transparent plastic substrates containing inorganic layers.

There is no particular limit to the method for forming a treatment layer. For example, wet coating method and dry coating method can be used. Examples of wet coating method include dip coating, spin coating, flow coating, spray coating, roll coating, photo concave coating, and the like. Examples of dry coating method include vacuum evaporation, sputtering, CVD, and the like. Specific examples of vacuum evaporation method include resistance heating, electron beam, high-frequency heating, ion beam, and the like. Examples of CVD method include plasma CVD, optical CVD, thermal CVD, and the like.

After forming a treatment layer on the substrate by a dry or wet coating method, heating, humidifying, light radiation, electron beam radiation, and the like can be carried out if necessary.

There is no particular limit to the thickness of the treatment layer formed by using a surface treatment agent containing the perfluorinated polyetheryl silane compound of the present invention. According to the dust proof, rubbing resistance and optical performance of optical components and screens of mobile phones and tablet computers, it is preferably 1-30 nm, more preferably 3-20 nm, and further preferably 5-10 nm.

When the surface treatment agent containing the above-mentioned perfluorinated polyetheryl silane compound of the present invention is used on the substrate such as various optical components (anti-reflective films, optical filters, optical lenses, eyeglass lenses, spectroscopic lenses, spectroscopes, prisms, mirrors, etc.) and the screens of mobile phones, a tablet computer, etc. to form a treatment layer, adhesion of dirt or moisture such as fingerprints, skin oil, sweat, cosmetics etc. may be prevented without degrading the optical properties of the optical elements and the screens. Even if dirt and moisture are adhered, they can be easily erased, and the treatment layer is scrape resistant, etc., thus resulting in that the treatment layer have excellent durability and can meet the requirements of anti-fouling, anti-fingerprint, scrape resistance, high smoothness and wear durability of optical components and cell phones, tablet computers, etc.

EXAMPLES

Synthesis Example 1

A perfluoropolyether group-containing silane compound A1 is synthesized according to the following steps Step 1:

10 g perfluoropolyether modified alcohol (a number average molecule weight of 3500~4000) with an average composition of $CF_3(OCF_2CF_2)_r(OCF_2)_sOCF_2CH_2OH$ (the sum of r, s is 35-42), 15 mL 1,3-bis(trifluoromethyl) benzene, 5 mL ethylene glycol dimethyl ether, 2.6 g 50 wt % potassium hydroxide solution are added into a 100-mL three-neck round-bottom flask equipped with a stirrer, and stirred at room temperature for 3 hours. 3.8 mL tert-butyl bromoacetate, and 0.42 g tetrabutylammonium bromide is then sequentially added into the reaction flask, and stirred at 50° C. for 5 hours. After extraction with water and decompression distillation, a colorless transparent product 9.6 g is obtained, i.e., an esteryl perfluoropolyether compound (M1): $CF_3(OCF_2CF_2)_r(OCF_2)_sOCF_2CH_2OCH_2COOC_4H_9$.

By identification with a NMR spectrometer, the characteristic $^1H$ chemical displacement of the newly-added structures is shown in the table below.

| Group structure | δ, ppm |
| --- | --- |
| $CH_2$— | 4.136 (s) |
| —$CF_2CH_2$— | 4.058~3.996 (q) |
| —$COOC_4H_9$ | 1.498 (s) |

Step 2:

9.6 g esteryl perfluoropolyether compound (M1) obtained in step 1, 17 g 10 wt % potassium hydroxide solution are added into a 100-mL three-neck round-bottom flask equipped with a thermometer and a stirrer, and stirred at 100° C. for 3 hours. After being reduced to room temperature, 10 mL tetrahydrofuran is added, and after being adjusted to be acidic with 2N hydrochloric acid, 30 mL hydrofluoroether HFE-7200 (produced by 3M Company) is added and stirred. The non-fluorine phase (i.e., the upper solution) is removed, and the fluorine phase is washed 2 times with 2N hydrochloric acid, and finally the colorless transparent product 9.0 g is obtained by decompression distillation, i.e., a carboxyl perfluorinated polyether compound (M2): $CF_3(OCF_2CF_2)_r(OCF_2)_s$ $OCF_2CH_2OCH_2COOH$.

By identification with a NMR spectrometer, the characteristic $^1H$ chemical displacement of the newly-added structures is shown in the table below.

| Group structure | δ, ppm |
| --- | --- |
| —$OCH_2$— | 4.308 (s) |
| —$CF_2CH_2$— | 4.063~4.001 (q) |

Step 3

9.0 g carboxyl perfluorinated polyether compound (M2) obtained in step 2 dissolved in 15 mL 1,3-bis(trifluoromethyl) benzene, 0.3 mL oxalol chloride, are added into a 100 mL four-neck round-bottom flask equipped with a drop funnel, a thermometer and a stirrer, 0.2 mL DMF dissolved in 5 mL 1,3-bis(trifluoromethyl) benzene is slowly added dropwise via the drop funnel, then warmed up to 50° C. and stirred for 4 hours. After reduced to room temperature, it is slowly added dropwise into a 250-mL three-neck round-bottom flask filled with 5 1,3-bis(trifluoromethyl) benzene, 4.2 mL diisopropyl ethylamine, 4 mL bis(3-trimethyloxy silyl propyl) amine, and stirred at room temperature for 5 hours. 40 mL perfluorohexane is added and extracted three times with 18 mL methanol. The fluorine phase is distilled under decompression to remove the volatile components to give a colorless to pale yellow product, i.e., the following perfluoropolyether group silane compound with trimethoxylsilane at the end (A1): $CF_3(OCF_2CF_2)_r(OCF_2)_sOCF_2CH_2OCH_2CON[(CH_2CH_2CH_2Si(OCH_3)_3)]_2$.

By identification with a NMR spectrometer, the characteristic $^1H$ chemical displacement of the newly-added structures is shown in the table below.

| Group structure | δ, ppm |
| --- | --- |
| —OCH$_2$— | 4.469 (s) |
| —CF$_2$CH$_2$— | 4.197~4.118 (q) |
| —Si(OCH$_3$)$_3$ | 3.658~3.636 (d) |
| —CH$_2$CH$_2$CH$_2$ Si(OCH$_3$)$_3$ | 3.477~3.262 (m) |
| —CH$_2$CH2CH$_2$Si(OCH$_3$)$_3$ | 1.868~1.769 (m) |
| —CH$_2$CH$_2$CH$_2$Si(OCH$_3$)$_3$ | 0.745~0.669 (m) |

Synthesis Example 2

A perfluoropolyether group-containing silane compound A2 is synthesized according to the following steps Step 1:

10 g perfluoropolyether modified alcohol (a number average molecule weight of 4500~5000) with an average composition of $CF_3(OCF_2CF_2)_r(OCF_2)_sOCF_2CH_2OH$ (a range of r+s is 35-42), 15 mL 1,3-bis(trifluoromethyl) benzene, 5 mL ethylene glycol dimethyl ether, 2.6 g 50 wt % potassium hydroxide solution are added into a 100-mL three-neck round-bottom flask equipped with a stirrer, and stirred at room temperature for 3 hours. 3.2 mL tert-butyl bromoacetate, and 0.32 g tetrabutylammonium bromide is then sequentially added into the reaction flask, and stirred at 50° C. for 5 hours. After extraction with water and decompression distillation, a colorless transparent product 9.6 g is obtained, i.e., an esteryl perfluoropolyether compound (M3): $CF_3(OCF_2CF_2)_r(OCF_2)_sOCF_2CH_2OCH_2COOC_4H_9$ By identification with a NMR spectrometer, the characteristic $^1H$ chemical displacement thereof is shown in the table below.

| Group structure | δ, ppm |
| --- | --- |
| —OCH$_2$— | 4.140 (s) |
| —CF$_2$CH$_2$— | 4.065~4.003 (q) |
| —COOC$_4$H$_9$ | 1.501 (s) |

Step 2:

9.6 g esteryl perfluoropolyether compound (M3) obtained by step 1, 17 g 10 wt % potassium hydroxide solution are added into a 100-mL three-neck round-bottom flask equipped with a thermometer and a stirrer, and stirred at 100° C. for 10 hours. After being reduced to room temperature, 10 mL tetrahydrofuran is added, and after being adjusted to be acidic with 15% hydrochloric acid, 30 mL hydrofluoroether HFE-7200 (produced by 3M Company) is added and stirred. The non-fluorine phase (i.e., the upper solution) is removed, the fluorine phase is washed 2 times with 2N hydrochloric acid, and finally the colorless transparent product 9.0 g is obtained by decompression distillation, i.e., a carboxyl perfluorinated polyether compound (M4): $CF_3(OCF_2CF_2)_r(OCF_2)_sOCF_2CH_2OCH_2COOH$.

By identification with a NMR spectrometer, the characteristic $^1H$ chemical displacement is shown in the table below.

| Group structure | δ, ppm |
| --- | --- |
| —OCH$_2$— | 4.310 (s) |
| —CF$_2$CH$_2$— | 4.069~3.998 (q) |

Step 3

9.0 g carboxyl perfluorinated polyether compound (M4) obtained in step 2 dissolved in 18 mL 1,3-bis(trifluoromethyl) benzene, 0.23 mL oxalol chloride, are added into a 100 mL four-neck round-bottom flask equipped with a drop funnel, a thermometer and a stirrer, 0.15 mL DMF dissolved in 5 mL 1,3-bis(trifluoromethyl) benzene is slowly added dropwise via the drop funnel, and then warmed up to 50° C. and stirred for 4 hours. After being reduced to room temperature, it is slowly added dropwise into a 250-mL three-neck round-bottom flask filled with 9 mL 1,3-bis(trifluoromethyl) benzene, 1.6 mL diisopropyl ethylamine, 2.9 mL bis(3-trimethyloxy silyl propyl) amine, and stirred at room temperature for 5 hours. 72 mL perfluorohexane is added and extracted three times with 43 mL methanol. The fluorine phase is distilled under decompression to remove the volatile components to give a colorless to pale yellow product, i.e., the following perfluoropolyether group silane compound with trimethoxylsilane at the end (A2): $CF_3(OCF_2CF_2)_r(OCF_2)_sOCF_2CH_2OCH_2CON[(CH_2)_3Si(OCH_3)_3]_2$.

By identification with a NMR spectrometer, the characteristic $^1H$ chemical displacement thereof is shown in the table below.

| Group structure | δ, ppm |
| --- | --- |
| —OCH$_2$— | 4.468 (s) |
| —CF$_2$CH$_2$— | 4.177~4.117 (m) |
| —Si(OCH$_3$)$_3$ | 3.656~3.634 (d) |
| —CH$_2$CH$_2$CH$_2$ Si(OCH$_3$)$_3$ | 3.468~3.270 (m) |
| —CH$_2$CH$_2$CH$_2$Si(OCH$_3$)$_3$ | 1.851~1.771 (m) |
| —CH$_2$CH$_2$CH$_2$Si(OCH$_3$)$_3$ | 0.730~0.667 (m) |

Synthesis Example 3

A perfluoropolyether group-containing silane compound A3 is synthesized according to the following steps Step 1:

3 g perfluoropolyether modified alcohol (the number average molecule weight of 3500~4000) with an average composition of $CF_3(OCF_2CF_2)_r(OCF_2)_sOCF_2CH_2OH$ (a range of r+s is 35-42), 9 mL 7200 and 3 mL t-BuOH solvent are added into a 100-mL three-neck round-bottom flask equipped with a stirrer, followed by addition of 0.45 g t-BuOK, and stirred at room temperature for 1.5 hours. 1.5 g $BrCH_2C_6H_4COOC_4H_9$, 0.12 g tetrabutylammonium bromide is then sequentially added into the reaction flask, and stirred at 50° C. for 1.5 hours. After extraction with water and decompression distillation, a colorless transparent liquid (M5) is obtained: $CF_3(OCF_2CF_2)_r(OCF_2)_sOCF_2CH_2OCH_2C_6H_4COOC_4H_9$.

The resulting colorless transparent liquid (M5) is added into a 100-mL three-neck round-bottom flask equipped with a thermometer and a stirrer, 9 mL 20 wt % potassium hydroxide solution is added and stirred at 115° C. for 5 hours. After being reduced to room temperature and adjusted to be acidic with 2N hydrochloric acid, the distilled water and tetrahydrofuran are added for extraction. The colorless transparent product 2.63 g is obtained by decompression distillation, i.e., a carboxyl perfluorinated polyether compound (M6): $CF_3(OCF_2CF_2)_r(OCF_2)_s$ $OCF_2CH_2OCH_2C_6H_4COOH$.

By identification with a NMR spectrometer, the characteristic $^1H$ chemical displacement thereof is shown in the table below.

| Group structure | δ, ppm |
| --- | --- |
| —$C_6H_4$— | 8.105 (d)/7.576 (d) |
| —$OCH_2$— | 4.949 (s) |
| —$CF_2CH_2$— | 4.099~4.040 (m) |

Step 2:

2.0 g carboxyl perfluorinated polyether compound (M6) dissolved in 6 mL 1,3-bis(trifluoromethyl) benzene, 70 μL oxalol chloride and 40 μl DMF, are added into a 100 mL four-neck round-bottom flask equipped with a drop funnel, a thermometer and a stirrer, and then warmed up to 50° C. and stirred for 5 hours. After being reduced to room temperature, it is slowly added dropwise into a 25 mL three-neck round-bottom flask filled with 2 mL 1,3-bis(trifluoromethyl) benzene, 0.72 mL triethylamine, 0.85 mL bis(3-trimethyloxy silyl propyl) amine, and stirred at room temperature for 5 hours. 10 mL perfluorohexane is added and extracted five times with 4 mL methanol. After being filtered with filtration membrane, it is distilled under reduced pressure to remove the volatile components to give a colorless transparent product 1.2 g, i.e., the following perfluoropolyether group silane compound with trimethoxylsilane at the end (A3): $CF_3(OCF_2CF_2)_r$ $(OCF_2)_sOCF_2CH_2OCH_2C_6H_4CON[(CH_2)_3Si(OCH_3)_3]_2$.

By identification with a NMR spectrometer, the characteristic $^1H$ chemical displacement thereof is shown in the table below.

| Group structure | δ, ppm |
| --- | --- |
| —$C_6H_4$— | 7.512 (m) |
| —$OCH_2$— | 4.872 (s) |
| —$CF_2CH_2$— | 4.014 (m) |
| —$Si(OCH_3)_3$/—$CH_2CH_2CH_2$— | 3.683~3.416 (m) |
| —$CH_2CH_2CH_2Si(OCH_3)_3$ | 1.985~1.787 (m) |
| —$CH_2CH_2CH_2Si(OCH_3)_3$ | 0.891~0.509 (m) |

Synthesis Example 4

A perfluoropolyether group-containing silane compound M2 is synthesized according to the following steps 1 g perfluoropolyether modified alcohol (the number average molecule weight of 3500~4000) with an average composition of $CF_3(OCF_2CF_2)_r(OCF_2)_sOCF_2CH_2OH$ (a range of r+s is 35-42), 1.5 mL 1,3-bis(trifluoromethyl) benzene, and 0.5 mL ethylene glycol dimethyl ether are added into a 100-mL three-neck round-bottom flask equipped with a stirrer, and stirred at room temperature, followed by addition of 0.09 g sodium hydride with bubble formation observed. 0.199 g $ClCH_2CN$, and 0.044 g tetrabutylammonium bromide are then sequentially added into the reaction flask, and stirred at 50° C. for 3 hours. 5 mL hydrofluoroether HFE-7200 is added, and a light yellow transparent solution is obtained via filtration of filtration membrane. After extraction with water and decompression distillation, a yellow-brown product (M7): $CF_3(OCF_2CF_2)_r(OCF_2)_s\ OCF_2CH_2OCH_2CN$, followed by addition of 3 g 20% potassium hydroxide solution and reflux hydrolysis at 115° C. 0.74 g product is given by acidification and purification, i.e., a carboxyl perfluoropolyether compound (M2): $CF_3(OCF_2CF_2)_r(OCF_2)_sOCF_2CH_2OCH_2COOH$.

By identification with a NMR spectrometer, the characteristic $^1H$ chemical displacement thereof is shown in the table below.

| Group structure | δ, ppm |
| --- | --- |
| —$CF_2CH_2$— | 4.063~4.001 (q) |
| —$OCH_2$— | 4.308 (s) |

By identification with a Fourier transform infrared spectrometer, the structural characteristics absorption peaks thereof is shown in the table below

| Group structure | ν, $cm^{-1}$ |
| --- | --- |
| —COOH | 2900~3100 (O—H stretch) |
| —COOH | 1739 (C=O stretch) |
| C—O/C—F | 1040~1335 (perfluoropolyether characteristic band) |

The resulting M2 may be further reacted as described in step 3 in Synthesis Example 1 to obtain A1: $CF_3(OCF_2CF_2)_r(OCF_2)_sOCF_2CH_2OCH_2CON[(CH_2CH_2CH_2Si(OCH_3)_3]_2$.

Examples 1-3

The synthesized compounds A1, A2 and A3 and hydrofluoroether (3M Company, Novec HFE7200) are formulated into 20% mass concentration as surface treatment agent (1), surface treatment agent (2) and surface treatment agent (3); the above surface treatment agents are vaporized onto a chemically reinforced glass by vacuum deposition. At a vacuum pressure of less than $4 \times 10^{-3}$ Pa, silicon dioxide is first deposited at a thickness of 10 nm to the chemically reinforced glass by electron beam deposition method to form a silicon dioxide membrane. The above surface treatment agens are deposited on each chemically reinforced glass at a thickness of about 8 to 10 nm is by vacuum deposition. Then, the chemically reinforced glass with the deposition film attached is solidified in an environment of 60% humidity and 70° C. for 2 hours to form a surface treatment layer.

Comparison Examples 1 to 3

The surface treatment layers are formed according to the same method as described in Example 1, excepting for replacing the surface treatment agents (1-3) formulated with the compounds A1, A2 and A3 with the following commercially available surface treatment agents 1 to 3.

Control surface treatment agent 1: Optool UD 509 (produced by Daikin Industries, Ltd.)

Control surface treatment agent 2: Optool DSX-E (produced by Daikin Industries, Ltd.)

Control surface treatment agent 3: X-71-195 (Shin-Etsu Chemical Co., Ltd.)

Comparison Example 4

The surface treatment agent is formulated and the surface treatment layer is formed according to the same method as described in Example 1, excepting for replacing compound (A1) with the following control compound 1.

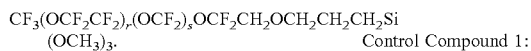
Control Compound 1.

Examples 4-6

The surface treatment agents (1-3) are dissolved in hydrofluoroether (3M Company, Novec HFE7200) at a 0.4% mass concentration to be prepared into the surface treatment agents (4-6); using a commercially available spray coating device, the surface treatment agents (4-6) are uniformly spray coated on chemically reinforced glass with a flow rate of 50 mg/sec and a conveying line speed of 13 mm/sec. Before coating, the chemically reinforced glass surface needs to be plasma treated. Then, the chemically reinforced glass with the spray treatment film attached is solidified in an environment of 60% humidity and 70° C. for 2 hours to form a surface treatment layer.

The surface treatment layer formed on the surface of the substrate is evaluated by the following methods. The results are shown in Tables 1 to 3.

1. Evaluation of Hydrophobicity and Oleophobicity

The contact angle of the surface treatment layer to water and the contact angle to n-hexadecane are measured using the contact angle measuring device (Beijing Harko Company, HARKE-DWA).

2. Determination of Smoothness

Using the friction coefficient instrument (Jinan Sanquan Zhongshi Company, MXS-05A), the dynamic friction coefficient of the relative public paper (Daboai) is tested under the following conditions.

Contact area: 63 mm×63 mm;
Load: 200 g
Line speed: 100 mm/min
Stroke: 30 mm

3. Evaluation of Abrasion Resistance

The water contact angle of the surface treatment layer after abrasion is evaluated using the abrasion tester (Taber Company, 5900) under the following conditions. After 1000 rounds for each time, the water contact angle is determined (when the water contact angle is less than 100 degrees or after being subjected to 20,000 frictions or steel wool damage, evaluation is terminated).

(1). Steel Wool Abrasion Resistance

Steel wool: BONSTAR #0000
Load: 1 kg/cm$^2$
Moving stroke: 40 mm
Moving speed: 60 rpm (2). Eraser Abrasion Resistance Eraser: Minoan MB006004, 6.0 mm
Load: 1 kg
Moving stroke: 40 mm
Moving speed: 40 rpm

TABLE 1

Hydrophobicity, oleophobicity and smoothness

| | Hydrophobicity (°) | Oleophobicity (°) | Dynamic friction coefficient |
|---|---|---|---|
| Example 1 | 117 | 70 | 0.03 |
| Example 2 | 116 | 76 | 0.04 |
| Example 3 | 116 | 76 | 0.04 |
| Example 4 | 116 | 68 | 0.04 |
| Example 5 | 116 | 69 | 0.05 |
| Example 6 | 113 | 70 | 0.05 |
| Comparison Example 1 | 115 | 69 | 0.04 |
| Comparison Example 2 | 114 | 68 | 0.07 |
| Comparison Example 3 | 117 | 68 | 0.03 |
| Comparison Example 4 | 115 | 68 | 0.03 |

TABLE 2

Steel wool abrasion resistance

Steel wool abrasion resistance (°)

| Friction times | Example 1 | Example 2 | Example 3 | Example 4 | Example 5 | Example 6 | Comparison Example 1 | Comparison Example 2 | Comparison Example 3 | Comparison Example 4 |
|---|---|---|---|---|---|---|---|---|---|---|
| 0 | 117 | 116 | 116 | 116 | 116 | 113 | 116 | 114 | 117 | 115 |
| 1000 | 116 | 114 | 114 | 116 | 114 | 112 | 115 | 111 | 116 | 112 |
| 2000 | 116 | 115 | 115 | 115 | 112 | 110 | 114 | 108 | 115 | 111 |
| 3000 | 116 | 114 | 114 | 115 | 110 | 113 | 114 | 108 | 115 | 108 |
| 4000 | 116 | 114 | 115 | 114 | 112 | 109 | 114 | 108 | 114 | 103 |
| 5000 | 115 | 113 | 112 | 114 | 110 | 112 | 113 | 106 | 114 | 97 |
| 6000 | 115 | 114 | 114 | 114 | 110 | 107 | 113 | 102 | 114 | — |
| 7000 | 115 | 113 | 109 | 113 | 111 | 111 | 113 | 99 | 114 | — |
| 8000 | 115 | 111 | 113 | 113 | 109 | 105 | 112 | — | 113 | — |
| 9000 | 115 | 111 | 111 | 113 | 110 | 100 | 112 | — | 113 | — |
| 10000 | 113 | 112 | 110 | 113 | 109 | 110 | 112 | — | 113 | — |
| 13000 | 113 | 111 | 111 | 112 | 109 | 111 | 112 | — | 113 | — |
| 16000 | 110 | 112 | 111 | 112 | 110 | 109 | 111 | — | 112 | — |
| 18000 | 109 | 110 | <100 | 110 | 109 | 98 | 110 | — | 111 | — |
| 20000 | 108 | 109 | — | 110 | 109 | 105 | 110 | — | 110 | — |

TABLE 3

Eraser abrasion resistance

Water contact angle (°)

| Friction times | Example 1 | Example 2 | Example 3 | Example 4 | Example 5 | Example 6 | Comparison Example 1 | Comparison Example 2 | Comparison Example 3 | Comparison Example 4 |
|---|---|---|---|---|---|---|---|---|---|---|
| 0 | 117 | 115 | 115 | 117 | 116 | 114 | 116 | 114.02 | 117 | 114 |
| 1000 | 116 | 113 | 113 | 114 | 113 | 112 | 113 | 109.1 | 113 | 103 |
| 2000 | 116 | 112 | 112 | 111 | 111 | 110 | 111 | 101.98 | 105 | 102 |
| 3000 | 115 | 113 | 113 | 110 | 107 | 108 | 108 | 97.18 | 93 | 94 |
| 4000 | 112 | 111 | 111 | 108 | 104 | 108 | 104 | — | — | — |
| 5000 | 112 | 112 | 112 | 108 | 84 | 107 | 84 | — | — | — |
| 6000 | 112 | 112 | 112 | 107 | — | 103 | — | — | — | — |
| 7000 | 109 | 108 | 108 | 106 | — | 97 | — | — | — | — |
| 8000 | 108 | 102 | 102 | 102 | — | — | — | — | — | — |

As can be seen from the above Examples, the surface treatment agent prepared by the perfluorinated polyether compound of the present invention makes the glass substrate treated be excellent in anti-fouling, anti-fingerprint, scrape resistant and abrasion resistant performances, and the comprehensive performance thereof is superior to that of the commercially available product. Moreover, the preparation of the compound of the present invention is simple in process, easy to operate and implement.

The above Examples are only for the purposes of illustrating the present invention, and are not limitations to the present invention. Ordinary technical persons in the relevant technical field may also make various changes and variation without departing from the scope of the present invention. Therefore, all equivalent technical solutions shall also belong to the scope disclosed in the invention.

The invention claimed is:

1. A perfluoropolyether group-containing silane compound represented by formula (3),

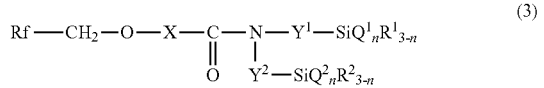

(3)

wherein,
Rf is $CF_3(OC_2F_4)_r(OCF_2)_sOCF_2$, wherein, r, s are independently integers of 0 or more and 200 or less, the sum of r and s is at least 1, the sequence of each repeating unit noted with r, s and bracketed with brackets is arbitrary in the formula;
in the formula, X is $C_{1-6}$ alkylidene, $—CH_2C_6H_4—$ or $—CH_2C_6H_4—$ which has a substituent on phenyl ring;
$Y^1$, $Y^2$ are independently $C_{1-6}$ alkylidene;
$Q^1$, $Q^2$ are independently hydroxyl or a group that can be hydrolyzed to hydroxyl group;
$R^1$, $R^2$ are independently $C_{1-6}$ alkyl or phenyl;
n is an integer of 1-3.

2. The perfluoropolyether group-containing silane compound according to claim 1, wherein when Rf is $CF_3(OC_2F_4)_r(OCF_2)_sOCF_2$, the sum of r and s is 20-100.

3. The perfluoropolyether group-containing silane compound according to claim 1, wherein n is 3.

4. The perfluoropolyether group-containing silane compound according to claim 1, wherein X is $—CH_2—$, $—CH(CH_3)—$ or $—CH_2C_6H_4—$.

5. The perfluoropolyether group-containing silane compound according to claim 1, wherein $Y^1$ and $Y^2$ are independently $—(CH_2)_3—$.

6. The perfluoropolyether group-containing silane compound according to claim 1, wherein $Q^1$, $Q^2$ are independently $C_{1-6}$ alkoxy.

7. The perfluoropolyether group-containing silane compound according to claim 1, wherein $Q^1$, $Q^2$ are independently $—OCH_3$, $—OCH(CH_3)_2$, $—OC_2H_5$ or $—OC_3H_7$.

8. The perfluoropolyether group-containing silane compound according to claim 1, wherein the silane compound has the number average molecule weight of 500~10,000.

9. A method for preparing a perfluoropolyether group-containing silane compound represented by the formula (3) of claim 1,

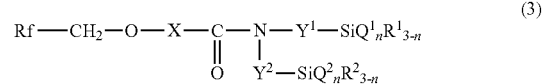

(3)

the method comprising: reacting Rf—$CH_2$—O—X—COOH with an acyl halogenation agent and an aminosilane coupling agent,

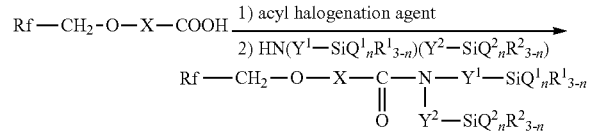

wherein, the definition of each symbol is the same as the definition of claim 1.

10. The method according to claim 9, wherein the acyl halogenation agent is $(COCl)_2$, $SOCl_2$, $POCl_3$, $PCl_5$ or $SOBr_2$.

11. The method according to claim 9, further comprising:
Step 1: first reacting the compound of formula Rf—$CH_2OH$ with a base in the presence of a solvent, and then making nucleophilic substitution reaction with a compound of formula L-X-G, wherein, L is a leaving group or atom where a nucleophilic substitution reaction can occur, G is a group that can be hydrolyzed to carboxylic acid; the definition of X is the same as claim 1; obtaining an esteryl perfluorinated polyether compound of formula Rf—$CH_2$—O—X-G

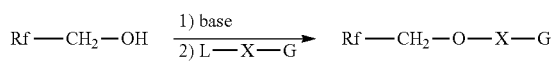

Step 2: hydrolyzing the compound of formula Rf—CH$_2$—O—X-G to obtain a carboxyl perfluorinated polyether compound of formula Rf—CH$_2$—O—X—COOH

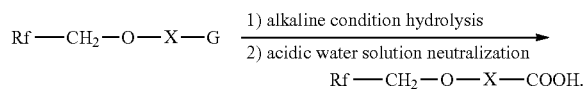

12. The method according to claim 11, wherein the base in step 1 is selected from inorganic base or organic base; the inorganic base is selected from at least one of LiOH, NaOH, KOH, K$_2$CO$_3$, Na$_2$CO$_3$, Cs$_2$CO$_3$, NaH, t-BuOK; the organic base is selected from at least one of DIPEA, DBU, or 1,1,3,3-tetramethylguanidine.

13. The method according to claim 11, wherein, in the compound of the formula L-X-G, L is chlorine atom, bromine atom, or iodine atom.

14. The method according to claim 11, wherein, in the compound of the formula L-X-G, G is ester group, nitrile group, or amide group.

15. The method according to claim 11, wherein the solvent is hydrofluoroether or fluorinated hydrocarbon.

16. The method according to claim 11, wherein the alkaline condition hydrolysis in step 2 uses a base selected from at least one of sodium hydroxide, potassium hydroxide, lithium hydroxide, cesium hydroxide.

17. The method according to claim 11, wherein the acidic water solution in step 2 comprises an inorganic acid.

18. The method according to claim 17, wherein the inorganic acid is hydrochloric acid, sulfuric acid, nitric acid or mixtures thereof.

19. The method according to claim 9, wherein the aminosilane coupling agent is bis(alkoxy silane alkyl)amine.

20. A surface treatment agent, comprising the perfluoropolyether group-containing silane compound of claim 1.

21. The surface treatment agent according to claim 20, wherein the surface treatment agent comprises a fluorinated solvent.

22. An article, wherein having a coating formed by the surface treatment agent of claim 21, and a water contact angle thereof is at least 110 degrees, and a dynamic friction coefficient is no more than 0.05.

23. The article according to claim 22, wherein the article is an optical component, a display screen of a smart phone, a tablet or computer.

24. The surface treatment agent according to claim 20, wherein the fluorinated solvent is hydrofluoroether.

25. The surface treatment agent according to claim 20, wherein the surface treatment agent contains 0.01-30 wt % perfluoropolyether group-containing silane compound.

26. The surface treatment agent according to claim 20, wherein the surface treatment agent contains 0.05-20 wt % perfluoropolyether group-containing silane compound.

27. The surface treatment agent according to claim 20, wherein the surface treatment agent contains 10-20 wt % perfluoropolyether group-containing silane compound.

* * * * *